United States Patent [19]

Cleuziat et al.

[11] Patent Number: 5,552,273
[45] Date of Patent: Sep. 3, 1996

[54] POLYPEPTIDES CONTAINING SEQUENCES CHARACTERISTIC OF PYRROLIDONE CARBOXYLYL PEPTIDASES, POLYNUCLEOTIDES CONTAINING A SEQUENCE CODING FOR SUCH POLYPEPTIDES, AND THEIR USE, IN PARTICULAR FOR DIAGNOSTIC PURPOSES

[75] Inventors: Philippe L. Cleuziat, Lyons; Abalo Awade, Rennes; Jeannine Robert-Baudouy, Rillieux La Pape; Jean-Pierre Gayral, Ambérieu en Bugey, all of France

[73] Assignee: Bio Merieux, L'Etoile, France

[21] Appl. No.: 107,684

[22] PCT Filed: Dec. 23, 1992

[86] PCT No.: PCT/FR92/01237

§ 371 Date: Oct. 18, 1993

§ 102(e) Date: Oct. 18, 1993

[30] Foreign Application Priority Data

Dec. 23, 1991 [FR] France .................................. 91 16059

[51] Int. Cl.$^6$ .............................. C12Q 1/68; C12P 21/06; C12N 1/20; C07H 19/00
[52] U.S. Cl. .............................. 435/6; 435/69.1; 435/195; 435/227; 435/320.1; 435/240.2; 435/252.3; 530/387.1; 536/22.1; 536/23.1; 536/23.2; 536/23.7
[58] Field of Search .............................. 435/6, 69.1, 195, 435/227, 320.1, 240.2, 252.3; 530/387.1; 536/22.1, 23.1, 23.2, 23.7

[56] References Cited

PUBLICATIONS

A. Szewczuk et al., "Pyrrolidonyl Peptidase in Bacteria", *European Journal Of Biochemistry*, vol. 8, 1969, pp. 63–67.
P. D. Ellner et al., "Preliminary Evaluation of a Rapid Colorimetric Method for the Presumptive Identification of Group A Streptococci and Enterococci," *Journal Of Clinical Microbiology*, vol. 22, No. 5, Nov. 1985, pp. 70–74.
A. Awade et al., "One Step Purification and Characterization of the Pyrrolidone Carboxyl Peptidase of *Streptococcus pyogenes* Over–expressed in *E. coli*", *Febs Letters*, vol. 308, No. 1, Aug. 1992, pp. 70–74.
A. Awade et al. "Characterization of the PCP Gene Encoding the Pyrrolidone Carboxyl Peptidase of *Bacillus subtilis*", *Febs Letters*, vol. 305, No. 1, Jun. 1992, pp. 67–73.
P. Cleuziat et al., "Molecular Characterization of PCP, the Structural Gene Encoding the Pyrrolidone Carboxylyl Peptidase from *Streptococcus pyogenes*", *Molecular Microbiology*, vol. 6, No. 15, 1992, pp. 2051–2063.
R. W. Armentrout et al., "Pyrrolidonecarboxylyl Peptidase: Stabilization and Purification", *Archives Of Biochemistry And Biophysics*, vol. 132, No. 1, Jun. 1969, pp. 80–90.
R. F. Doolittle, "Pyrrolidonecarboxylyl Peptidase", Methods In Enzymology, vol. 19, 1970, pp. 555–569.
Kauthold et al "Few minute tests for the identificati . . . " Zentralbl Bakteriol. 272 (2) 1989 pp. 191–195.
Glover "Principles of cloning DNA" Gene Cloning pp. 1–20 1984.
Lerner "Tapping the immunological repertoire . . . " Nature 299 (14) pp. 592–596 1982.

*Primary Examiner*—Robert A. Wax
*Assistant Examiner*—Hyosuk Kim
*Attorney, Agent, or Firm*—Oliff & Berridge

[57] ABSTRACT

Purified polypeptides containing characteristic sequences common to the pyrrolidone carboxylyl peptidases (PYRases) of bacteria, for example of *Streptococcus pyogenes*, or containing fragments of these sequences; antibodies recognizing these polypeptides; polynucleotides coding for such polypeptides or fragments.

Application, in particular, to the overproduction of PYRases by inserting a polynucleotide coding for a PYRase into a vector, and then culturing a host cell transformed using such a vector, or to the production of nucleic acid probes specific for a bacterium having a PYRase gene, expressed or otherwise. These nucleic acid probes may be used as capture or detection probes according to conventional hybridization techniques.

17 Claims, 14 Drawing Sheets

```
5'..AA CAA AAT AAA AGA ACT TAC CTA TTT TCC ATC CAA AAT GTT TAG CAA TCA   48

TCA TCT GCA AGG CAA CGT ATT GCA TGG CAT TGA TGT GAT GAG CAA CTA ATA TGT  104

CAT TAG AAC GTT GCG TCA AAC TAG CAT CTA AAT AAA GAT CGA AAT GCA GTT ATC  158
                                                                Pb-35
AAA AAT GCA AGC TCC TAT CGG CCC TTG TTT TAA TTA TTA CTC ACATG CCT TAA    212
              Pa-35                            Pa-10          +1
TGT ATT TAC TTG CTT ATT ATT AAC TTT TTT GCT AAG TTA GTA GCG TCA GTT ATT  266
                  Pb-10       →                  ←       YR2        →
       SD               Met Lys Ile Leu Val Thr Gly Phe Asp Pro Phe Gly
CAT TGA AAG GAC ATT ATT[ATG]AAA ATT CTT GTA ACA GGC TTT GAT CCC TTT GGC  320
                                                  ←         YM1

Gly Glu Ala Ile Asn Pro Ala Leu Glu Ala Ile Lys Lys Leu Pro Ala Thr Ile
GGC GAA GCT ATT AAT CCT GCC CTT GAA GCT ATC AAG AAA TTG CCA GCA ACC ATT  374

His Gly Ala Glu Ile Lys Cys Ile Glu Val Pro Thr Val Phe Gln Lys Ser Ala
CAT GGA GCA GAA ATC AAA TGT ATT GAA GTT CCA ACG GTT TTT CAA AAA TCT GCC  428

Asp Val Leu Gln Gln His Ile Glu Ser Phe Gln Pro Asp Ala Val Leu Cys Ile
GAT GTG CTC CAG CAG CAT ATC GAA AGC TTT CAA CCT GAT GCA GTC CTT TGT ATT  482

Gly Gln Ala Gly Gly Arg Thr Gly Leu Thr Pro Glu Arg Val Ala Ile Asn Gln
GGG CAA GCT GGT GGC CGG ACT GGA CTA ACG CCA GAA CGC GTT GCC ATT AAT CAA  536

Asp Asp Ala Arg Ile Pro Asp Asn Glu Gly Asn Gln Pro Ile Asp Thr Pro Ile
GAC GAT GCT CGC ATT CCT GAT AAC GAA GGG AAT CAG CCT ATT GAT ACA CCT ATT  590

Arg Ala Asp Gly Lys Ala Ala Tyr Phe Ser Thr Leu Pro Ile Lys Ala Met Val
CGT GCA GAT GGT AAA GCA GCT TAT TTT TCA ACC TTG CCA ATC AAA GCG ATG GTT  644

Ala Ala Ile His Gln Ala Gly Leu Pro Ala Ser Val Ser Asn Thr Ala Gly Thr
GCT GCC ATT CAT CAG GCT GGG CTT CCT GCT TCT GTT TCT AAT ACA GCT GGT ACC  698

Phe Val Cys Asn His Leu Met Tyr Gln Ala Leu Tyr Leu Val Asp Lys Tyr Cys
TTT GTT TGC AAT CAT TTG ATG TAT CAA GCC CTT TAC TTA GTG GAT AAA TAT TGT  752

Pro Asn Ala Lys Ala Gly Phe Met His Ile Pro Phe Met Met Glu Gln Val Val
CCA AAT GCC AAA GCT GGG TTT ATG CAT ATT CCC TTT ATG ATG GAA CAG GTT GTT  806
            ↙        YU5

Asp Lys Pro Asn Thr Ala Ala Met Asn Leu Asp Asp Ile Thr Arg Gly Ile Glu
GAT AAA CCT AAT ACA GCT GCC ATG AAC CTC GAT GAT ATT ACA AGA GGA ATT GAG  860

Ala Ala Ile Phe Ala Ile Val Asp Phe Lys Asp Arg Ser Asp Leu Lys Arg Val
GCT GCT ATT TTT GCC ATT GTC GAT TTC AAA GAT CGT TCC GAT TTA AAA CGT GTA  914
                                                              AflIII
```

FIG.3A

```
                Gly Gly Ala Thr His
                GGG GGC GCT ACT CAC TGA CTG TGA CGC TAC TAA ACC TAT TTT AAA AAA ACA GAG   968
                    STEM-LOOP
                ATA TGA ACT AAC TCT GTT TTT TTT GTG CTA AAA ATG AAA GAC CTA GGG AAA CTT  1022
                      *** ***
                TTC ATC GGT CTT TCT CAA TTG TCA TCT TAA TCT AAT ACT ACT TCT AAC ATC AGC  1076

GGG TAT AGT TTG CCA GTA ATT AAG AAA CGT TGT TGA TCT AAA TGA GCA ATC CCA  1130

TTC AAA ACA TTA AGG TCA GGG TAA TGG GAC TTA TCA AGA TTT AAG GCT TTT AAC  1184

AAA GGA CTA ATA TCA TAG GTG GCT ACC ACC TTT CCA GAA TCA GGT TGG AGT TTG  1238

ACA ATA GTA TTG GTT TGC CAA ATA TTG GCA TAG AGA TAA CCA TCT ACA TAC TCT  1292
                                        SspI
                AAT TCG TTA AGC ATT GAG ATA GGG ACA CTT TCT ATA GCA ACT AGT...3'         1337
```

FIG. 3B

```
5'...ATG AGA AAA AAA GTG CTG ATC ACA GGC TTT GAC CCT TTT GAC AAA GAA ACC GTC      54
    Met Arg Lys Lys Val Leu Ile Thr Gly Phe Asp Pro Phe Asp Lys Glu Thr Val

AAT CCA TCA TGG GAA GCG GCG AAA CGG CTT AAT GGC TTC GAG ACA GAA GAA GCC      108
    Asn Pro Ser Trp Glu Ala Ala Lys Arg Leu Asn Gly Phe Glu Thr Glu Glu Ala

ATT ATT ACA GCG GAA CAA ATT CCA ACC GTC TTT AGA TCC GCT CTG GAC ACT CTG      162
    Ile Ile Thr Ala Glu Gln Ile Pro Thr Val Phe Arg Ser Ala Leu Asp Thr Leu

CGC CAA GCC ATT CAA AAA CAT CAG CCA GAT ATC GTA ATT TGT GTC GGC CAA GCA      216
    Arg Gln Ala Ile Gln Lys His Gln Pro Asp Ile Val Ile Cys Val Gly Gln Ala

GGA GGA CGG ATG CAG ATT ACA CCG GAA CGA GTG GCA ATC AAC CTT GCA GAT GCG      270
    Gly Gly Arg Met Gln Ile Thr Pro Glu Arg Val Ala Ile Asn Leu Ala Asp Ala

CGA ATC CCC GAT AAC GAA GGA CAT CAG CCG ATT GAT GAA GAG ATT TCT CCA GAT      324
    Arg Ile Pro Asp Asn Glu Gly His Gln Pro Ile Asp Glu Glu Ile Ser Pro Asp

GGG CCC GCC GCT TAC TGG ACA AGG CTT CCC GTG AAA CGA ATG ACT GCT AAG ATG      378
    Gly Pro Ala Ala Tyr Trp Thr Arg Leu Pro Val Lys Arg Met Thr Ala Lys Met

AAG GAA CAC GGC ATT CCA GCT GCG GTT TCC TAC ACA GCG GGG ACC TTT GTA TGC      432
    Lys Glu His Gly Ile Pro Ala Ala Val Ser Tyr Thr Ala Gly Thr Phe Val Cys

AAC TAT TTG TTC TAC GGG TTA ATG GAT CAC ATT AGC CGG ACA TCC CCA CAC ATT      486
    Asn Tyr Leu Phe Tyr Gly Leu Met Asp His Ile Ser Arg Thr Ser Pro His Ile

CGC GGC GGT TTT ATT CAT ATT CCT TAC ATT CCG CAG CAA ACA ATC GAC AAA ACA      540
    Arg Gly Gly Phe Ile His Ile Pro Tyr Ile Pro Gln Gln Thr Ile Asp Lys Thr

GCG CCG AGC CTC AGC CTG GAC ACG ATT GTC CGG GCA TTG AGA ATC GCC GCT GTT      594
    Ala Pro Ser Leu Ser Leu Asp Thr Ile Val Arg Ala Leu Arg Ile Ala Ala Val

ACG GCC GCA CAA TAT GAT GAG GAT GTG AAG TCA CCG GGT GGT ACG CTG CAC ...3'   645
    Thr Ala Ala Gln Tyr Asp Glu Asp Val Lys Ser Pro Gly Gly Thr Leu His
```

FIG.5

```
5'... ATG CGA ATT GTA CTG CTG ACG GGT TTC GAA CCC TTT GAT CAA GAC CCG GTG AAC    54
      Met Arg Ile Val Leu Leu Thr Gly Phe Glu Pro Phe Asp Gln Asp Pro Val Asn

CCC TCC TGG GAA GCT GTG CGC CAA CTG GAT GGC GTG CAG TTG GGA AGC GAC GTG   108
      Pro Ser Trp Glu Ala Val Arg Gln Leu Asp Gly Val Gln Leu Gly Ser Asp Val

AAG ATT GTT GCG CGC CGG CTG CCT TGT GCA TTT GCC ACG GCG GGT GAA TGC CTG   162
      Lys Ile Val Ala Arg Arg Leu Pro Cys Ala Phe Ala Thr Ala Gly Glu Cys Leu

ACC CGG CTG ATC GAC GAG TTG CAC CCG GCG ATG GTG ATC GCC ACC GGA TTG GGG   216
      Thr Arg Leu Ile Asp Glu Leu His Pro Ala Met Val Ile Ala Thr Gly Leu Gly

CCG GGG CGT AGC GAT ATC TCA GTC GAA CGG GTG GCG ATC AAC ATC AAT GAT GCA   270
      Pro Gly Arg Ser Asp Ile Ser Val Glu Arg Val Ala Ile Asn Ile Asn Asp Ala

CGC ATC CCC GAT AAT CTG GGT GAG CAG CCT ATC GAT ACG GCA GTC GTG GCT GAC   324
      Arg Ile Pro Asp Asn Leu Gly Glu Gln Pro Ile Asp Thr Ala Val Val Ala Asp

GGC CCG GCG GCT TTT TTC ACG ACG CTG CCG ATC AAG GCG ATG GTC AAG GCC GTG   378
      Gly Pro Ala Ala Phe Phe Thr Thr Leu Pro Ile Lys Ala Met Val Lys Ala Val

CGT GAA GCG GGA ATC GCG GCC TCG GTA TCG CAG ACG GCA GGG ACG TTC GTG TGT   432
      Arg Glu Ala Gly Ile Ala Ala Ser Val Ser Gln Thr Ala Gly Thr Phe Val Cys

AAT CAG GTT TTT TAT CTG CTG CAG CAT GCG CTC GCA GGG TCT GGG GTA CGC AGT   486
      Asn Gln Val Phe Tyr Leu Leu Gln His Ala Leu Ala Gly Ser Gly Val Arg Ser

GGG TTT ATC CAC GTG CCG TTT CTG CCG GAG CAG GTG GCG GGT TCG CAG CGG CCC   540
      Gly Phe Ile His Val Pro Phe Leu Pro Glu Gln Val Ala Gly Ser Gln Arg Pro

TCG ATG GCA CTG GAT GCA ATG GTT GCG GGA TTG CAG GCG GCT GTA CTG ACA GCT   594
      Ser Met Ala Leu Asp Ala Met Val Ala Gly Leu Gln Ala Ala Val Leu Thr Ala

TGG CAT ACA CCG GTG GAT GTC AAA GAA GCG GGC GGG CAG GTC AGC ...3'         639
      Trp His Thr Pro Val Asp Val Lys Glu Ala Gly Gly Gln Val Ser
```

FIG.6

```
  1 Met Arg Lys Lys Val Leu Ile Thr Gly Phe Asp Pro Phe Asp Lys Glu Thr  17
              |   :   |   |   :   |   |   |   |   |   |   :   |   |   .
          1 Met Lys Ile Leu Val Thr Gly Phe Asp Pro Phe Gly Gly Glu Ala  15

18 Val Asn Pro Ser Trp Glu Ala Ala Lys Arg Leu Asn Gly Phe Glu Thr Glu  34
      :   |   |   .   :   |   |   |   :   |   :       .   .   .
 16 Ile Asn Pro Ala Leu Glu Ala Ile Lys Lys Leu Pro Ala  -  Thr Ile His  31

35 Glu Ala Ile Ile Thr Ala Glu Gln Ile Pro Thr Val Phe Arg Ser Ala Leu  51
      :   |   |   .   .   :   :   |   |   |   |   .   .   .
 32 Gly Ala Glu Ile Lys Cys Ile Glu Val Pro Thr Val Phe Gln Lys Ser Ala  48

52 Asp Thr Leu Arg Gln Ala Ile Gln Lys His Gln Pro Asp Ile Val Ile Cys  68
      |   .   |   .   |   |   :   .   |   |   |   |   |   :   |
 49 Asp Val Leu Gln Gln His Ile Glu Ser Phe Gln Pro Asp Ala Val Leu Cys  65

69 Val Gly Gln Ala Gly Gly Arg Met Gln Ile Thr Pro Glu Arg Val Ala Ile  85
      :   |   |   |   |   |   |   .   :   |   |   |   |   |   |   |
 66 Ile Gly Gln Ala Gly Gly Arg Thr Gly Leu Thr Pro Glu Arg Val Ala Ile  82

86 Asn Leu Ala Asp Ala Arg Ile Pro Asp Asn Glu Gly His Gln Pro Ile Asp 102
      |   .   |   |   |   |   |   |   |   |   |   :   |   |   |
 83 Asn Gln Asp Asp Ala Arg Ile Pro Asp Asn Glu Gly Asn Gln Pro Ile Asp  99

103 Glu Glu Ile Ser Pro Asp Gly Pro Ala Ala Tyr Trp Thr Arg Leu Pro Val 119
      .   .   |   .   :   |   |   .   |   |   :   .   .   |   |   |
100 Thr Pro Ile Arg Ala Asp Gly Lys Ala Ala Tyr Phe Ser Thr Leu Pro Ile 116

120 Lys Arg Met Thr Ala Lys Met Lys Glu His Gly Ile Pro Ala Ala Val Ser 136
      |   |   .   |   :   .   :       |   :   |   |   .   |   |
117 Lys Ala Met Val Ala Ala Ile His Gln Ala Gly Leu Pro Ala Ser Val Ser 133

137 Tyr Thr Ala Gly Thr Phe Val Cys Asn Tyr Leu Phe Tyr Gly Leu Met Asp 153
      |   |   |   |   |   |   |   |   .   |   :   |   .   :
134 Asn Thr Ala Gly Thr Phe Val Cys Asn His Leu Met Tyr Gln Ala Leu Tyr 150

154 His Ile Ser Arg Thr Ser Pro His Ile Arg Gly Gly Phe Ile His Ile Pro 170
      :   .   :       :   |   :   :   :   |   |   :   |   |   |
151 Leu Val Asp Lys Tyr Cys Pro Asn Ala Lys Ala Gly Phe Met His Ile Pro 167

171 Tyr Ile Pro Gln Gln Thr Ile Asp Lys Thr  -  Ala Pro Ser Leu Ser Leu 186
      :   :       :   .   :   |   |   .       .   .   :   .   |
168 Phe Met Met Glu Gln Val Val Asp Lys Pro Asn Thr Ala Ala Met Asn Leu 184
```

FIG.8A

```
187 Asp Thr Ile Val Arg Ala Leu Arg Ile Ala Ala Val Thr Ala Ala Gln Tyr 203
     |   .   |   .   |   :   :           |   .   .   .   :   :
185 Asp Asp Ile Thr Arg Gly Ile Glu Ala Ala Ile Phe Ala Ile Val Asp Phe 201

204 Asp Glu  -   -  Asp Val Lys Ser Pro Gly Gly Thr Leu His 215
     .   :           |   :   |   .   .   |   |   .       |
202 Lys Asp Arg Ser Asp Leu Lys Arg Val Gly Gly Ala Thr His 215
```

FIG.8B

```
1       Met Lys Ile Leu Val Thr Gly Phe Asp Pro Phe Gly Gly Glu Ala  15
        Met Arg Ile Val Leu Leu Thr Gly Phe Glu Pro Phe Asp Gln Asp Pro
        Met Arg Lys Lys Val Leu Ile Thr Gly Phe Asp Pro Phe Asp Lys Glu Thr
                        Leu  X  Thr Gly Phe  X  Pro Phe

16  Ile Asn Pro Ala Leu Glu Ala Ile Lys Lys Leu Pro Ala Thr Ile His Gly  32
    Val Asn Pro Ser Trp Glu Ala Val Arg Gln Leu Asp Gly Val Gln Leu Gly
    Val Asn Pro Ser Trp Glu Ala Ala Lys Arg Leu Asn Gly Phe Glu Thr Glu

33  Ala Glu Ile Lys Cys Ile Glu  -   -  Val Pro Thr Val Phe Gln Lys Ser  47
    Ser Asp Val Lys Ile Val Ala Arg Arg Leu Pro Cys Ala Phe Ala Thr Ala
    Glu Ala Ile  -  Ile Thr Ala Glu Gln Ile Pro Thr Val Phe Arg Ser Ala

48  Ala Asp Val Leu Gln Gln His Ile Glu Ser Phe Gln Pro Asp Ala Val Leu  64
    Gly Glu Cys Leu Thr Arg Leu Ile Asp Glu Leu His Pro Ala Met Val Ile
    Leu Asp Thr Leu Arg Gln Ala Ile Gln Lys His Gln Pro Asp Ile Val Ile

65  Cys Ile Gly Gln Ala Gly Gly Arg Thr Gly Leu Thr Pro Glu Arg Val Ala  81
    Ala Thr Gly Leu Gly Pro Gly Arg Ser Asp Ile Ser Val Glu Arg Val Ala
    Cys Val Gly Gln Ala Gly Gly Arg Met Gln Ile Thr Pro Glu Arg Val Ala
                                                  Glu Arg Val Ala

82  Ile Asn Gln Asp Asp Ala Arg Ile Pro Asp Asn Glu Gly Asn Gln Pro Ile  98
    Ile Asn Ile Asn Asp Ala Arg Ile Pro Asp Asn Leu Gly Glu Gln Pro Ile
    Ile Asn Leu Ala Asp Ala Arg Ile Pro Asp Asn Glu Gly His Gln Pro Ile
    Ile Asn  X   X  Asp Ala Arg Ile Pro Asp Asn  X  Gly  X  Gln Pro Ile

99  Asp Thr Pro Ile Arg Ala Asp Gly Lys Ala Ala Tyr Phe Ser Thr Leu Pro  115
    Asp Thr Ala Val Val Ala Asp Gly Pro Ala Ala Phe Phe Thr Thr Leu Pro
    Asp Glu Glu Ile Ser Pro Asp Gly Pro Ala Ala Tyr Trp Thr Arg Leu Pro
    Asp

116 Ile Lys Ala Met Val Ala Ala Ile His Gln Ala Gly Leu Pro Ala Ser Val  132
    Ile Lys Ala Met Val Lys Ala Val Arg Glu Ala Gly Ile Ala Ala Ser Val
    Val Lys Arg Met Thr Ala Lys Met Lys Glu His Gly Ile Pro Ala Ala Val
                                                                    Val

133 Ser Asn Thr Ala Gly Thr Phe Val Cys Asn His Leu Met Tyr  -  Gln Ala  148
    Ser Gln Thr Ala Gly Thr Phe Val Cys Asn Gln Val Phe Tyr  -  Leu Leu
    Ser Tyr Thr Ala Gly Thr Phe Val Cys Asn Tyr Leu Phe Tyr Gly Leu Met
    Ser  X  Thr Ala Gly Thr Phe Val Cys Asn
```

FIG.9A

```
149  Leu Tyr Leu Val Asp Lys Tyr Cys  -  Pro Asn Ala Lys Ala Gly Phe Met  164
     Gln His Ala Leu Ala Gly Ser Gly  -  Val  -   -  Arg Ser Gly Phe Ile
     Asp His Ile Ser Arg Thr Ser Pro His Ile  -   -  Arg Gly Gly Phe Ile

165  His Ile Pro Phe Met Met Glu Gln Val Val Asp Lys Pro Asn Thr Ala Ala  181
     His Val Pro Phe Leu Pro Glu Gln Val Ala Gly Ser  -  Gln Arg Pro Ser
     His Ile Pro Tyr Ile Pro Gln Gln Thr Ile Asp Lys  -  Thr Ala Pro Ser

182  Met Asn Leu Asp Asp Ile Thr Arg Gly Ile Glu Ala Ala Ile Phe Ala Ile  198
     Met Ala Leu Asp Ala Met Val Ala Gly Leu Gln Ala Ala Val Leu Thr Ala
     Leu Ser Leu Asp Thr Ile Val Arg Ala Leu Arg Ile Ala Ala Val Thr Ala

199  Val Asp Phe Lys Asp Arg Ser Asp Leu Lys Arg Val Gly Gly Ala Thr His  215
     Trp His Thr Pro Val Asp Val Lys Glu Ala Gly Gly Gln Val Ser
     Ala Gln Tyr Asp Glu Asp Val Lys Ser Pro Gly Gly Thr Leu His
```

FIG.9B

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 1336 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 284..928

( x i ) SEQUENCE DESCRIPTION: SEQ ID NO:1:

-continued

```
AACAAAATAA AAGAACTTAC CTATTTTCCA TCCAAAATGT TTAGCAATCA TCATCTGCAA        60

GGCAACGTAT TGCATGGCAT TGATGTGATG AGCAACTAAT ATGTCATTAG AACGTTGCGT       120

CAAACTAGCA TCTAAATAAA GATCGAAATG CAGTTATCAA AAATGCAAGC TCCTATCGGC       180

CCTTGTTTTA ATTATTACTC ACATGCCTTA ATGTATTTAC TTGCTTATTA TTAACTTTTT       240

TGCTAAGTTA GTAGCGTCAG TTATTCATTG AAAGGACATT ATT ATG AAA ATT CTT        295
                                              Met Lys Ile Leu
                                               1
```

| | | | | | | | | | | | | | | | | |
|---|---|---|---|---|---|---|---|---|---|---|---|---|---|---|---|---|
| GTA | ACA | GGC | TTT | GAT | CCC | TTT | GGC | GGC | GAA | GCT | ATT | AAT | CCT | GCC | CTT | 343 |
| Val | Thr | Gly | Phe | Asp | Pro | Phe | Gly | Gly | Glu | Ala | Ile | Asn | Pro | Ala | Leu | |
| 5 | | | | 10 | | | | | 15 | | | | | 20 | | |
| GAA | GCT | ATC | AAG | AAA | TTG | CCA | GCA | ACC | ATT | CAT | GGA | GCA | GAA | ATC | AAA | 391 |
| Glu | Ala | Ile | Lys | Lys | Leu | Pro | Ala | Thr | Ile | His | Gly | Ala | Glu | Ile | Lys | |
| | | | 25 | | | | | 30 | | | | | 35 | | | |
| TGT | ATT | GAA | GTT | CCA | ACG | GTT | TTT | CAA | AAA | TCT | GCC | GAT | GTG | CTC | CAG | 439 |
| Cys | Ile | Glu | Val | Pro | Thr | Val | Phe | Gln | Lys | Ser | Ala | Asp | Val | Leu | Gln | |
| | | | 40 | | | | | 45 | | | | | 50 | | | |
| CAG | CAT | ATC | GAA | AGC | TTT | CAA | CCT | GAT | GCA | GTC | CTT | TGT | ATT | GGG | CAA | 487 |
| Gln | His | Ile | Glu | Ser | Phe | Gln | Pro | Asp | Ala | Val | Leu | Cys | Ile | Gly | Gln | |
| | | 55 | | | | | 60 | | | | | 65 | | | | |
| GCT | GGT | GGC | CGG | ACT | GGA | CTA | ACG | CCA | GAA | CGC | GTT | GCC | ATT | AAT | CAA | 535 |
| Ala | Gly | Gly | Arg | Thr | Gly | Leu | Thr | Pro | Glu | Arg | Val | Ala | Ile | Asn | Gln | |
| | 70 | | | | | 75 | | | | | 80 | | | | | |
| GAC | GAT | GCT | CGC | ATT | CCT | GAT | AAC | GAA | GGG | AAT | CAG | CCT | ATT | GAT | ACA | 583 |
| Asp | Asp | Ala | Arg | Ile | Pro | Asp | Asn | Glu | Gly | Asn | Gln | Pro | Ile | Asp | Thr | |
| 85 | | | | 90 | | | | | 95 | | | | | 100 | | |
| CCT | ATT | CGT | GCA | GAT | GGT | AAA | GCA | GCT | TAT | TTT | TCA | ACC | TTG | CCA | ATC | 631 |
| Pro | Ile | Arg | Ala | Asp | Gly | Lys | Ala | Ala | Tyr | Phe | Ser | Thr | Leu | Pro | Ile | |
| | | | 105 | | | | | 110 | | | | | 115 | | | |
| AAA | GCG | ATG | GTT | GCT | GCC | ATT | CAT | CAG | GCT | GGG | CTT | CCT | GCT | TCT | GTT | 679 |
| Lys | Ala | Met | Val | Ala | Ala | Ile | His | Gln | Ala | Gly | Leu | Pro | Ala | Ser | Val | |
| | | | 120 | | | | | 125 | | | | | 130 | | | |
| TCT | AAT | ACA | GCT | GGT | ACC | TTT | GTT | TGC | AAT | CAT | TTG | ATG | TAT | CAA | GCC | 727 |
| Ser | Asn | Thr | Ala | Gly | Thr | Phe | Val | Cys | Asn | His | Leu | Met | Tyr | Gln | Ala | |
| | | 135 | | | | | 140 | | | | | 145 | | | | |
| CTT | TAC | TTA | GTG | GAT | AAA | TAT | TGT | CCA | AAT | GCC | AAA | GCT | GGG | TTT | ATG | 775 |
| Leu | Tyr | Leu | Val | Asp | Lys | Tyr | Cys | Pro | Asn | Ala | Lys | Ala | Gly | Phe | Met | |
| | 150 | | | | | 155 | | | | | 160 | | | | | |
| CAT | ATT | CCC | TTT | ATG | ATG | GAA | CAG | GTT | GTT | GAT | AAA | CCT | AAT | ACA | GCT | 823 |
| His | Ile | Pro | Phe | Met | Met | Glu | Gln | Val | Val | Asp | Lys | Pro | Asn | Thr | Ala | |
| 165 | | | | 170 | | | | | 175 | | | | | 180 | | |
| GCC | ATG | AAC | CTC | GAT | GAT | ATT | ACA | AGA | GGA | ATT | GAG | GCT | GCT | ATT | TTT | 871 |
| Ala | Met | Asn | Leu | Asp | Asp | Ile | Thr | Arg | Gly | Ile | Glu | Ala | Ala | Ile | Phe | |
| | | | 185 | | | | | 190 | | | | | 195 | | | |
| GCC | ATT | GTC | GAT | TTC | AAA | GAT | CGT | TCC | GAT | TTA | AAA | CGT | GTA | GGG | GGC | 919 |
| Ala | Ile | Val | Asp | Phe | Lys | Asp | Arg | Ser | Asp | Leu | Lys | Arg | Val | Gly | Gly | |
| | | | 200 | | | | | 205 | | | | | 210 | | | |
| GCT | ACT | CAC | TGACTGTGAC GCTACTAAAC CTATTTTAAA AAAACAGAGA | | | | | | | | | | | | 968 |
| Ala | Thr | His | | | | | | | | | | | | | | |
| | | 215 | | | | | | | | | | | | | | |

```
TATGAACTAA CTCTGTTTTT TTTGTGCTAA AAATGAAAGA CCTAGGGAAA CTTTTCATCG      1028

GTCTTTCTCA ATTGTCATCT TAATCTAATA CTACTTCTAA CATCAGCGGG TATAGTTTGC      1088

CAGTAATTAA GAAACGTTGT TGATCTAAAT GAGCAATCCC ATTCAAAACA TTAAGGTCAG      1148

GGTAATGGGA CTTATCAAGA TTTAAGGCTT TTAACAAAGG ACTAATATCA TAGGTGGCTA      1208

CCACCTTTCC AGAATCAGGT TGGAGTTTGA CAATAGTATT GGTTTGCCAA ATATTGGCAT      1268

AGAGATAACC ATCTACATAC TCTAATTCGT TAAGCATTGA GATAGGGACA CTTTCTATAG      1328
```

CAACTAGT 1336

( 2 ) INFORMATION FOR SEQ ID NO:2:

( i ) SEQUENCE CHARACTERISTICS:
        ( A ) LENGTH: 645 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..645

( x i ) SEQUENCE DESCRIPTION: SEQ ID NO:2:

```
ATG AGA AAA AAA GTG CTG ATC ACA GGC TTT GAC CCT TTT GAC AAA GAA        48
Met Arg Lys Lys Val Leu Ile Thr Gly Phe Asp Pro Phe Asp Lys Glu
 1               5                  10                  15

ACC GTC AAT CCA TCA TGG GAA GCG GCG AAA CGG CTT AAT GGC TTC GAG        96
Thr Val Asn Pro Ser Trp Glu Ala Ala Lys Arg Leu Asn Gly Phe Glu
             20                  25                  30

ACA GAA GAA GCC ATT ATT ACA GCG GAA CAA ATT CCA ACC GTC TTT AGA       144
Thr Glu Glu Ala Ile Ile Thr Ala Glu Gln Ile Pro Thr Val Phe Arg
         35                  40                  45

TCC GCT CTG GAC ACT CTG CGC CAA GCC ATT CAA AAA CAT CAG CCA GAT       192
Ser Ala Leu Asp Thr Leu Arg Gln Ala Ile Gln Lys His Gln Pro Asp
     50                  55                  60

ATC GTA ATT TGT GTC GGC CAA GCA GGA GGA CGG ATG CAG ATT ACA CCG       240
Ile Val Ile Cys Val Gly Gln Ala Gly Gly Arg Met Gln Ile Thr Pro
 65                  70                  75                  80

GAA CGA GTG GCA ATC AAC CTT GCA GAT GCG CGA ATC CCC GAT AAC GAA       288
Glu Arg Val Ala Ile Asn Leu Ala Asp Ala Arg Ile Pro Asp Asn Glu
                 85                  90                  95

GGA CAT CAG CCG ATT GAT GAA GAG ATT TCT CCA GAT GGG CCC GCC GCT       336
Gly His Gln Pro Ile Asp Glu Glu Ile Ser Pro Asp Gly Pro Ala Ala
            100                 105                 110

TAC TGG ACA AGG CTT CCC GTG AAA CGA ATG ACT GCT AAG ATG AAG GAA       384
Tyr Trp Thr Arg Leu Pro Val Lys Arg Met Thr Ala Lys Met Lys Glu
        115                 120                 125

CAC GGC ATT CCA GCT GCG GTT TCC TAC ACA GCG GGG ACC TTT GTA TGC       432
His Gly Ile Pro Ala Ala Val Ser Tyr Thr Ala Gly Thr Phe Val Cys
    130                 135                 140

AAC TAT TTG TTC TAC GGG TTA ATG GAT CAC ATT AGC CGG ACA TCC CCA       480
Asn Tyr Leu Phe Tyr Gly Leu Met Asp His Ile Ser Arg Thr Ser Pro
145                 150                 155                 160

CAC ATT CGC GGC GGT TTT ATT CAT ATT CCT TAC ATT CCG CAG CAA ACA       528
His Ile Arg Gly Gly Phe Ile His Ile Pro Tyr Ile Pro Gln Gln Thr
                165                 170                 175

ATC GAC AAA ACA GCG CCG AGC CTC AGC CTG GAC ACG ATT GTC CGG GCA       576
Ile Asp Lys Thr Ala Pro Ser Leu Ser Leu Asp Thr Ile Val Arg Ala
            180                 185                 190

TTG AGA ATC GCC GCT GTT ACG GCC GCA CAA TAT GAT GAG GAT GTG AAG       624
Leu Arg Ile Ala Ala Val Thr Ala Ala Gln Tyr Asp Glu Asp Val Lys
        195                 200                 205

TCA CCG GGT GGT ACG CTG CAC                                           645
Ser Pro Gly Gly Thr Leu His
    210                 215
```

( 2 ) INFORMATION FOR SEQ ID NO:3:

( i ) SEQUENCE CHARACTERISTICS:
        ( A ) LENGTH: 639 base pairs ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..639

( x i ) SEQUENCE DESCRIPTION: SEQ ID NO:3:

| ATG | CGA | ATT | GTA | CTG | CTG | ACG | GGT | TTC | GAA | CCC | TTT | GAT | CAA | GAC | CCG | 48 |
| Met | Arg | Ile | Val | Leu | Leu | Thr | Gly | Phe | Glu | Pro | Phe | Asp | Gln | Asp | Pro | |
| 1 | | | | 5 | | | | | 10 | | | | | 15 | | |
| GTG | AAC | CCC | TCC | TGG | GAA | GCT | GTG | CGC | CAA | CTG | GAT | GGC | GTG | CAG | TTG | 96 |
| Val | Asn | Pro | Ser | Trp | Glu | Ala | Val | Arg | Gln | Leu | Asp | Gly | Val | Gln | Leu | |
| | | | 20 | | | | | 25 | | | | | 30 | | | |
| GGA | AGC | GAC | GTG | AAG | ATT | GTT | GCG | CGC | CGG | CTG | CCT | TGT | GCA | TTT | GCC | 144 |
| Gly | Ser | Asp | Val | Lys | Ile | Val | Ala | Arg | Arg | Leu | Pro | Cys | Ala | Phe | Ala | |
| | | 35 | | | | | 40 | | | | | 45 | | | | |
| ACG | GCG | GGT | GAA | TGC | CTG | ACC | CGG | CTG | ATC | GAC | GAG | TTG | CAC | CCG | GCG | 192 |
| Thr | Ala | Gly | Glu | Cys | Leu | Thr | Arg | Leu | Ile | Asp | Glu | Leu | His | Pro | Ala | |
| | 50 | | | | | 55 | | | | | 60 | | | | | |
| ATG | GTG | ATC | GCC | ACC | GGA | TTG | GGG | CCG | GGG | CGT | AGC | GAT | ATC | TCA | GTC | 240 |
| Met | Val | Ile | Ala | Thr | Gly | Leu | Gly | Pro | Gly | Arg | Ser | Asp | Ile | Ser | Val | |
| 65 | | | | | 70 | | | | | 75 | | | | | 80 | |
| GAA | CGG | GTG | GCG | ATC | AAC | ATC | AAT | GAT | GCA | CGC | ATC | CCC | GAT | AAT | CTG | 288 |
| Glu | Arg | Val | Ala | Ile | Asn | Ile | Asn | Asp | Ala | Arg | Ile | Pro | Asp | Asn | Leu | |
| | | | | 85 | | | | | 90 | | | | | 95 | | |
| GGT | GAG | CAG | CCT | ATC | GAT | ACG | GCA | GTC | GTG | GCT | GAC | GGC | CCG | GCG | GCT | 336 |
| Gly | Glu | Gln | Pro | Ile | Asp | Thr | Ala | Val | Val | Ala | Asp | Gly | Pro | Ala | Ala | |
| | | | 100 | | | | | 105 | | | | | 110 | | | |
| TTT | TTC | ACG | ACG | CTG | CCG | ATC | AAG | GCG | ATG | GTC | AAG | GCC | GTG | CGT | GAA | 384 |
| Phe | Phe | Thr | Thr | Leu | Pro | Ile | Lys | Ala | Met | Val | Lys | Ala | Val | Arg | Glu | |
| | | 115 | | | | | 120 | | | | | 125 | | | | |
| GCG | GGA | ATC | GCG | GCC | TCG | GTA | TCG | CAG | ACG | GCA | GGG | ACG | TTC | GTG | TGT | 432 |
| Ala | Gly | Ile | Ala | Ala | Ser | Val | Ser | Gln | Thr | Ala | Gly | Thr | Phe | Val | Cys | |
| | 130 | | | | | 135 | | | | | 140 | | | | | |
| AAT | CAG | GTT | TTT | TAT | CTG | CTG | CAG | CAT | GCG | CTC | GCA | GGG | TCT | GGG | GTA | 480 |
| Asn | Gln | Val | Phe | Tyr | Leu | Leu | Gln | His | Ala | Leu | Ala | Gly | Ser | Gly | Val | |
| 145 | | | | | 150 | | | | | 155 | | | | | 160 | |
| CGC | ACT | GGG | TTT | ATC | CAC | GTG | CCG | TTT | CTG | CCG | GAG | CAG | GTG | GCG | GGT | 528 |
| Arg | Thr | Gly | Phe | Ile | His | Val | Pro | Phe | Leu | Pro | Glu | Gln | Val | Ala | Gly | |
| | | | | 165 | | | | | 170 | | | | | 175 | | |
| TCG | CAG | CGG | CCC | TCG | ATG | GCA | CTG | GAT | GCA | ATG | GTT | GCG | GGA | TTG | CAG | 576 |
| Ser | Gln | Arg | Pro | Ser | Met | Ala | Leu | Asp | Ala | Met | Val | Ala | Gly | Leu | Gln | |
| | | | 180 | | | | | 185 | | | | | 190 | | | |
| GCG | GCT | GTA | CTG | ACA | GCT | TGG | CAT | ACA | CCG | GTG | GAT | GTC | AAA | GAA | GCG | 624 |
| Ala | Ala | Val | Leu | Thr | Ala | Trp | His | Thr | Pro | Val | Asp | Val | Lys | Glu | Ala | |
| | | 195 | | | | | 200 | | | | | 205 | | | | |
| GGC | GGG | CAG | GTC | AGC | | | | | | | | | | | | 639 |
| Gly | Gly | Gln | Val | Ser | | | | | | | | | | | | |
| | 210 | | | | | | | | | | | | | | | |

( 2 ) INFORMATION FOR SEQ ID NO:4:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( x i ) SEQUENCE DESCRIPTION: SEQ ID NO:4:

```
Glu Arg Val Ala Ile Asn Xaa Xaa Asp Ala Arg Ile Pro Asp Asn Xaa
1               5                   10                  15

Gly Xaa Gln Pro Ile Asp
            20
```

(2) INFORMATION FOR SEQ ID NO:5:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:5:

```
Gly Xaa Xaa Ala Xaa Val Ser Xaa Thr Ala Gly Thr Phe Val Cys Asn
1               5                   10                  15

Xaa Xaa Xaa Tyr
            20
```

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:6:

```
Leu Xaa Thr Gly Phe Xaa Pro Phe
1               5
```

(2) INFORMATION FOR SEQ ID NO:7:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 2..3
        (D) OTHER INFORMATION: /label=Z
            / note="Each independently of one another
            represents Ala, Val, Leu, Ile, Pro, Trp, Phe or
            Met"

(ix) FEATURE:
        (A) NAME/KEY: Peptide
        (B) LOCATION: 8
        (D) OTHER INFORMATION: /label=Z
            / note="Each independently of one another,
            represents Gly, Ser, Thr, Tyr, Gys, Asn or Gln"

(ix) FEATURE:
        (A) NAME/KEY: Peptide
        (B) LOCATION: 17
        (D) OTHER INFORMATION: /label=Z
            / note="Each independently of one another,
            represents Gly, Ser, Thr, Tyr, Cys, Asn, Gln, Lys,
            Arg or His"

(ix) FEATURE:
        (A) NAME/KEY: Peptide
        (B) LOCATION: 18..19
        (D) OTHER INFORMATION: /label=Z
            / note="Each independently of one another
            represents Ala, Val, Leu, Ile, Pro, Trp, Phe or
            Met"

( x i ) SEQUENCE DESCRIPTION: SEQ ID NO:7:

```
Gly Glx Glx Ala Xaa Val Ser Glx Thr Ala Gly Thr Phe Val Cys Asn
 1               5                   10                  15
Glx Glx Glx Tyr
            20
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 2
        ( D ) OTHER INFORMATION: /label=Z
            / note="Each independently of one another,
            represents Ala, Val, Leu, Ile, Pro, Trp, Phe or
            Met"

( i x ) FEATURE:
        ( A ) NAME/KEY: Peptide
        ( B ) LOCATION: 6
        ( D ) OTHER INFORMATION: /label=Z
            / note="Each independently of one another,
            represents Gly, Ser, Thr, Tyr, Cys, Asn, Gln, Ala,
            Asp or Glu"

( x i ) SEQUENCE DESCRIPTION: SEQ ID NO:8:

```
Leu Glx Thr Gly Phe Glx Pro Phe
 1               5
```

( 2 ) INFORMATION FOR SEQ ID NO:9:

( i ) SEQUENCE CHARACTERISTICS:
        ( A ) LENGTH: 215 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Met Arg Lys Lys Val Leu Ile Thr Gly Phe Asp Pro Phe Asp Lys Glu
 1               5                   10                  15
Thr Val Asn Pro Ser Trp Glu Ala Ala Lys Arg Leu Asn Gly Phe Glu
                20                  25                  30
Thr Glu Glu Ala Ile Ile Thr Ala Glu Gln Ile Pro Thr Val Phe Arg
            35                  40                  45
Ser Ala Leu Asp Thr Leu Arg Gln Ala Ile Gln Lys His Gln Pro Asp
        50                  55                  60
Ile Val Ile Cys Val Gly Gln Ala Gly Gly Arg Met Gln Ile Thr Pro
65                  70                  75                  80
Glu Arg Val Ala Ile Asn Leu Ala Asp Ala Arg Ile Pro Asp Asn Glu
                85                  90                  95
Gly His Gln Pro Ile Asp Glu Glu Ile Ser Pro Asp Gly Pro Ala Ala
            100                 105                 110
Tyr Trp Thr Arg Leu Pro Val Lys Arg Met Thr Ala Lys Met Lys Glu
            115                 120                 125
His Gly Ile Pro Ala Ala Val Ser Tyr Thr Ala Gly Thr Phe Val Cys
        130                 135                 140
Asn Tyr Leu Phe Tyr Gly Leu Met Asp His Ile Ser Arg Thr Ser Pro
145                 150                 155                 160
```

```
His  Ile  Arg  Gly  Gly  Phe  Ile  His  Ile  Pro  Tyr  Ile  Pro  Gln  Gln  Thr
               165                      170                     175

Ile  Asp  Lys  Thr  Ala  Pro  Ser  Leu  Ser  Leu  Asp  Thr  Ile  Val  Arg  Ala
               180                      185                     190

Leu  Arg  Ile  Ala  Ala  Val  Thr  Ala  Gln  Tyr  Asp  Glu  Asp  Val  Lys
          195                      200                     205

Ser  Pro  Gly  Gly  Thr  Leu  His
     210                      215
```

(2) INFORMATION FOR SEQ ID NO:10:

(i) SEQUENCE CHARACTERISTICS:
        (A) LENGTH: 215 amino acids
        (B) TYPE: amino acid
        (D) TOPOLOGY: linear (ii) MOLECULE TYPE: peptide (xi) SEQUENCE DESCRIPTION: SEQ ID NO:10:

```
Met  Lys  Ile  Leu  Val  Thr  Gly  Phe  Asp  Pro  Phe  Gly  Gly  Glu  Ala  Ile
1                   5                   10                      15

Asn  Pro  Ala  Leu  Glu  Ala  Ile  Lys  Lys  Leu  Pro  Ala  Thr  Ile  His  Gly
               20                  25                          30

Ala  Glu  Ile  Lys  Cys  Ile  Glu  Val  Pro  Thr  Val  Phe  Gln  Lys  Ser  Ala
          35                  40                          45

Asp  Val  Leu  Gln  Gln  His  Ile  Glu  Ser  Phe  Gln  Pro  Asp  Ala  Val  Leu
     50                  55                      60

Cys  Ile  Gly  Gln  Ala  Gly  Gly  Arg  Thr  Gly  Leu  Thr  Pro  Glu  Arg  Val
65                  70                      75                          80

Ala  Ile  Asn  Gln  Asp  Asp  Ala  Arg  Ile  Pro  Asp  Asn  Glu  Gly  Asn  Gln
               85                      90                          95

Pro  Ile  Asp  Thr  Pro  Ile  Arg  Ala  Asp  Gly  Lys  Ala  Ala  Tyr  Phe  Ser
               100                     105                     110

Thr  Leu  Pro  Ile  Lys  Ala  Met  Val  Ala  Ala  Ile  His  Gln  Ala  Gly  Leu
          115                     120                     125

Pro  Ala  Ser  Val  Ser  Asn  Thr  Ala  Gly  Thr  Phe  Val  Cys  Asn  His  Leu
     130                     135                     140

Met  Tyr  Gln  Ala  Leu  Tyr  Leu  Val  Asp  Lys  Tyr  Cys  Pro  Asn  Ala  Lys
145                     150                     155                     160

Ala  Gly  Phe  Met  His  Ile  Pro  Phe  Met  Met  Glu  Gln  Val  Val  Asp  Lys
               165                     170                     175

Pro  Asn  Thr  Ala  Ala  Met  Asn  Leu  Asp  Asp  Ile  Thr  Arg  Gly  Ile  Glu
               180                     185                     190

Ala  Ala  Ile  Phe  Ala  Ile  Val  Asp  Phe  Lys  Asp  Arg  Ser  Asp  Leu  Lys
          195                     200                     205

Arg  Val  Gly  Gly  Ala  Thr  His
     210                     215
```

(2) INFORMATION FOR SEQ ID NO:11:

(i) SEQUENCE CHARACTERISTICS:
        (A) LENGTH: 215 amino acids
        (B) TYPE: amino acid
        (D) TOPOLOGY: linear (ii) MOLECULE TYPE: peptide (xi) SEQUENCE DESCRIPTION: SEQ ID NO:11:

```
Met  Lys  Ile  Leu  Val  Thr  Gly  Phe  Asp  Pro  Phe  Gly  Gly  Glu  Ala  Ile
```

```
  1                   5                         10                        15

Asn  Pro  Ala  Leu  Glu  Ala  Ile  Lys  Lys  Leu  Pro  Ala  Thr  Ile  His  Gly
               20                       25                      30

Ala  Glu  Ile  Lys  Cys  Ile  Glu  Val  Pro  Thr  Val  Pro  Gln  Lys  Ser  Ala
          35                       40                      45

Asp  Val  Leu  Gln  Gln  His  Ile  Glu  Ser  Phe  Gln  Pro  Asp  Ala  Val  Leu
     50                       55                      60

Cys  Ile  Gly  Gln  Ala  Gly  Gly  Arg  Thr  Gly  Leu  Thr  Pro  Glu  Arg  Val
65                       70                      75                           80

Ala  Ile  Asn  Gln  Asp  Asp  Ala  Arg  Ile  Pro  Asp  Asn  Glu  Gly  Asn  Gln
                    85                      90                           95

Pro  Ile  Asp  Thr  Pro  Ile  Arg  Ala  Asp  Gly  Lys  Ala  Ala  Tyr  Phe  Ser
               100                      105                     110

Thr  Leu  Pro  Ile  Lys  Ala  Met  Val  Ala  Ala  Ile  His  Gln  Ala  Gly  Leu
          115                      120                     125

Pro  Ala  Ser  Val  Ser  Asn  Thr  Ala  Gly  Thr  Phe  Val  Cys  Asn  His  Leu
     130                      135                     140

Met  Tyr  Gln  Ala  Leu  Tyr  Leu  Val  Asp  Lys  Tyr  Cys  Pro  Asn  Ala  Lys
145                      150                     155                          160

Ala  Gly  Phe  Met  His  Ile  Pro  Phe  Met  Met  Glu  Gln  Val  Val  Asp  Lys
                    165                     170                          175

Pro  Asn  Thr  Ala  Ala  Met  Asn  Leu  Asp  Asp  Ile  Thr  Arg  Gly  Ile  Glu
               180                      185                     190

Ala  Ala  Ile  Phe  Ala  Ile  Val  Asp  Phe  Lys  Asp  Arg  Ser  Asp  Leu  Lys
          195                      200                     205

Arg  Val  Gly  Gly  Ala  Thr  His
     210                      215
```

( 2 ) INFORMATION FOR SEQ ID NO:12:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Met  Arg  Ile  Val  Leu  Leu  Thr  Gly  Phe  Glu  Pro  Phe  Asp  Gln  Asp  Pro
1                   5                       10                      15

Val  Asn  Pro  Ser  Trp  Glu  Ala  Val  Arg  Gln  Leu  Asp  Gly  Val  Gln  Leu
               20                      25                      30

Gly  Ser  Asp  Val  Lys  Ile  Val  Ala  Arg  Arg  Leu  Pro  Cys  Ala  Phe  Ala
          35                      40                      45

Thr  Ala  Gly  Glu  Cys  Leu  Thr  Arg  Leu  Ile  Asp  Glu  Leu  His  Pro  Ala
     50                      55                      60

Met  Val  Ile  Ala  Thr  Gly  Leu  Gly  Pro  Gly  Arg  Ser  Asp  Ile  Ser  Val
65                       70                      75                           80

Glu  Arg  Val  Ala  Ile  Asn  Ile  Asn  Asp  Ala  Arg  Ile  Pro  Asp  Asn  Leu
                    85                      90                           95

Gly  Glu  Gln  Pro  Ile  Asp  Thr  Ala  Val  Val  Ala  Asp  Gly  Pro  Ala  Ala
               100                     105                     110

Phe  Phe  Thr  Thr  Leu  Pro  Ile  Lys  Ala  Met  Val  Lys  Ala  Val  Arg  Glu
          115                     120                     125

Ala  Gly  Ile  Ala  Ala  Ser  Val  Ser  Gln  Thr  Ala  Gly  Thr  Phe  Val  Cys
     130                     135                     140
```

```
Asn Gln Val Phe Tyr Leu Leu Gln His Ala Leu Ala Gly Ser Gly Val
145                 150                 155                 160

Arg Ser Gly Phe Ile His Val Pro Phe Leu Pro Glu Gln Val Ala Gly
                165                 170                 175

Ser Gln Arg Pro Ser Met Ala Leu Asp Ala Met Val Ala Gly Leu Gln
            180                 185                 190

Ala Ala Val Leu Thr Ala Trp His Thr Pro Val Asp Val Lys Glu Ala
        195                 200                 205

Gly Gly Gln Val Ser
        210
```

(2) INFORMATION FOR SEQ ID NO:13:

(i) SEQUENCE CHARACTERISTICS:
        (A) LENGTH: 215 amino acids
        (B) TYPE: amino acid
        (D) TOPOLOGY: linear (ii) MOLECULE TYPE: peptide (xi) SEQUENCE DESCRIPTION: SEQ ID NO:13:

```
Met Arg Lys Lys Val Leu Ile Thr Gly Phe Asp Pro Phe Asp Lys Glu
1               5                   10                  15

Thr Val Asn Pro Ser Trp Glu Ala Ala Lys Arg Leu Asn Gly Phe Glu
            20                  25                  30

Thr Glu Glu Ala Ile Ile Thr Ala Glu Gln Ile Pro Thr Val Phe Arg
        35                  40                  45

Ser Ala Leu Asp Thr Leu Arg Gln Ala Ile Gln Lys His Gln Pro Asp
    50                  55                  60

Ile Val Ile Cys Val Gly Gln Ala Gly Gly Arg Met Gln Ile Thr Pro
65                  70                  75                  80

Glu Arg Val Ala Ile Asn Leu Ala Asp Ala Arg Ile Pro Asp Asn Glu
                85                  90                  95

Gly His Gln Pro Ile Asp Glu Glu Ile Ser Pro Asp Gly Pro Ala Ala
            100                 105                 110

Tyr Trp Thr Arg Leu Pro Val Lys Arg Met Thr Ala Lys Met Lys Glu
        115                 120                 125

His Gly Ile Pro Ala Ala Val Ser Tyr Thr Ala Gly Thr Phe Val Cys
    130                 135                 140

Asn Tyr Leu Phe Tyr Gly Leu Met Asp His Ile Ser Arg Thr Ser Pro
145                 150                 155                 160

His Ile Arg Gly Gly Phe Ile His Ile Pro Tyr Ile Pro Gln Gln Thr
                165                 170                 175

Ile Asp Lys Thr Ala Pro Ser Leu Ser Leu Asp Thr Ile Val Arg Ala
            180                 185                 190

Leu Arg Ile Ala Ala Val Thr Ala Ala Gln Tyr Asp Glu Asp Val Lys
        195                 200                 205

Ser Pro Gly Gly Thr Leu His
    210                 215
```

(2) INFORMATION FOR SEQ ID NO:14:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:14:

```
Leu  Xaa  Thr  Gly  Phe  Xaa  Pro  Phe  Glu  Arg  Val  Ala  Ile  Asn  Xaa  Xaa
 1              5              10                            15

Asp  Ala  Arg  Ile  Pro  Asp  Asn  Xaa  Gly  Xaa  Gln  Pro  Ile  Asp  Val  Ser
              20                        25                        30

Xaa  Thr  Ala  Gly  Thr  Phe  Val  Cys  Asn
          35                        40
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AATAGCTTCG CCGCCAAAGG GATCAAAGCC      30

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ACAGGCTTTG ATCCCTTTGG      20

( 2 ) INFORMATION FOR SEQ ID NO:17:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Gln  Pro  Asp  Ala  Val  Leu  Cys  Ile  Gly  Gln  Ala  Gly  Gly  Arg  Thr  Gly
 1              5                        10                            15

Leu  Thr  Pro  Glu  Arg  Val  Ala  Ile  Asn  Gln  Asp  Asp  Ala  Arg  Ile  Pro
              20                        25                        30

Asp  Asn  Glu  Gly  Asn  Gln  Pro  Ile  Asp
          35                        40
```

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Gly  Leu  Pro  Ala  Ser  Val  Ser  Asn  Thr  Ala  Gly  Thr  Phe  Val  Cys  Asn
 1              5                        10                            15

His  Leu  Met  Tyr
          20
```

(2) INFORMATION FOR SEQ ID NO:19:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:19:

```
Cys Pro Asn Ala Lys Ala Gly Phe Met His Ile Pro Phe Met
1               5                   10
```

(2) INFORMATION FOR SEQ ID NO:20:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:20:

```
Lys Ile Leu Val Thr Gly Phe Asp Pro Phe Gly
1               5                   10
```

(2) INFORMATION FOR SEQ ID NO:21:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:21:

```
Glu Arg Val Ala Ile Asn Gln Asp Asp Ala Arg Ile Pro Asp Asn Glu
1               5                   10                  15

Gly Asn Gln Pro Ile Asp
                20
```

(2) INFORMATION FOR SEQ ID NO:22:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:22:

```
Val Ser Asn Thr Ala Gly Thr Phe Val Cys Asn
1               5                   10
```

(2) INFORMATION FOR SEQ ID NO:23:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:23:

```
Gln Pro Asp Ala Val Leu Cys Ile Gly Gln Ala Gly Gly Arg Thr Gly
1               5                   10                  15

Leu Thr Pro Glu Arg Val Ala Ile Asn Gln Asp Asp Ala Arg Ile Pro
                20                  25                  30
```

```
          Asp  Asn  Glu  Gly  Asn  Gln  Pro  Ile  Asp
                    35                       40
```

(2) INFORMATION FOR SEQ ID NO:24:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:24:

```
Gly  Leu  Pro  Ala  Ser  Val  Ser  Asn  Thr  Ala  Gly  Thr  Phe  Val  Cys  Asn
1                   5                        10                       15

His  Leu  Met  Tyr
              20
```

(2) INFORMATION FOR SEQ ID NO:25:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:25:

```
Cys  Pro  Asn  Ala  Lys  Ala  Gly  Phe  Met  His  Ile  Pro  Phe  Met
1                   5                        10
```

(2) INFORMATION FOR SEQ ID NO:26:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:26:

```
Lys  Ile  Leu  Val  Thr  Gly  Phe  Asp  Pro  Phe  Gly
1                   5                        10
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TTCTGGCGTT AGTCCAGTCC                      20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TATCAGGAAT GCGAGCATCG                      20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TGCATAAACC CAGCTTTGGC     20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TTGCCAGCAA CCATTCATGG     20

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

AGAAACAGAA GCAGGAAGCC     20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

AAAATCTGCC GATGTGCTCC     20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CTTTGTATTG GGCAAGCTGG     20

( 2 ) INFORMATION FOR SEQ ID NO:34:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:34:

TACTGGCAAA CTATACCCGC 20

(2) INFORMATION FOR SEQ ID NO:35:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

TGCTCGCATT CCTGATAACG 20

(2) INFORMATION FOR SEQ ID NO:36:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

ATCAAAGCGA TGGTTGCTGC 20

(2) INFORMATION FOR SEQ ID NO:37:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

CCCTATCTCA ATGCTTAACG 20

(2) INFORMATION FOR SEQ ID NO:38:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

TCAAAAATCT GCCGATGTGC 20

(2) INFORMATION FOR SEQ ID NO:39:

(i) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:39:

AGGAAGCCCA GCCTGATGAA 20

( 2 ) INFORMATION FOR SEQ ID NO:40:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:40:

CAGCTTATTT TTCAACCTTG CC 22

( 2 ) INFORMATION FOR SEQ ID NO:41:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:41:

CAAAGCGATG GTTGCTGCCA 20

( 2 ) INFORMATION FOR SEQ ID NO:42:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

ATGAAAATTC TTGTAACAGG C 21

( 2 ) INFORMATION FOR SEQ ID NO:43:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

GTGAGTAGCG CCCCCTAC 18

POLYPEPTIDES CONTAINING SEQUENCES CHARACTERISTIC OF PYRROLIDONE CARBOXYLYL PEPTIDASES, POLYNUCLEOTIDES CONTAINING A SEQUENCE CODING FOR SUCH POLYPEPTIDES, AND THEIR USE, IN PARTICULAR FOR DIAGNOSTIC PURPOSES

The present invention relates to polypeptides containing sequences characteristic of pyrrolidone carboxylyl peptidases, to polynucleotides containing a sequence coding for such polypeptides, and to their use, in particular for diagnostic purposes.

Pyrrolidone carboxylyl peptidases are exopeptidases which specifically remove 2-pyrrolidone-5-carboxylic acid (PCA) residues from the $NH_2$-terminal end of polypeptide chains and proteins (Doolittle and Armentrout, Biochemistry, 1968, 7, 516–521). These enzymes are also referred to as pyrrolidonyl peptidases (Szewczuk and Mulczyk, Eur. J. Biochem, 1969, 8, 63–67) or more commonly PYRases (Mitchell et al., Diagn. Microbiol. Infect. Dis., 1987, 6, 283–286). These enzymes are specific for the L-PCA-L-amino acid optical isomers (Uliana and Doolittle, Arch. Biochem. Biophys., 1969, 131, 561–656), and the rate of hydrolysis depends on the amino acid adjacent to the PCA residue (Fujiwara et al., Biochim. Biophys. Acta, 1979, 570, 140–148). These enzymes also belong to the arylamidase group, since they are capable of hydrolysing the peptide bond of the synthetic chromogenic substrate L-pyroglutamyl-β-naphthylamide (Patterson et al., J. Biol. Chem., 1963, 238, 3611–3620). These enzymes were first described in bacteria (Mulczyk and Szewczuk, J. Gen. Microb., 1970, 61, 9–13), but they are also found to be present in animal and plant tissues and in man (Szewczuk and Kwiatkowska, Eur. J. Biochem., 1970, 15, 92–96). PYRases prove, in addition, to be a specific means for removing PCA residues blocking the $NH_2$-terminal end of peptides, and to be very useful for determining the amino acid sequence of proteins, since peptides not possessing a free α-$NH_2$ group cannot be sequenced according to the usual Edman degradation. The biochemical and physicochemical properties of PYRases are quite well known, since they have been studied for more than about twenty years. Enzymes having PYRase activity have been isolated and partially purified from several microorganisms, in particular from bacteria such as *Pseudomonas fluorescens* (Armentrout and Doolittle, Arch. Biochem. Biophys., 1969, 132, 80–90; Doolittle, Meth. Enzymol. 1970, 19, 555–569), *Bacillus subtilis* (Szewczuk and Mulczyk, Eur. J. Biochem., 1969, 8, 63–67), Bacillus amyloliquefaciens (Tsuru etal., J. Biochem, 1978, 84, 467–476), Klebsiella cloacas (Kwiatkowska et al., J. Biol. Chem., 1974, 249, 7729–7736) and *Enterococcus faecium* (Sullivan etal., Aust. J. Biol. Sci., 1977, 30, 543–552). Conventional purification methods have not, to date, enabled the pyrrolidone carboxylyl peptidases to be purified to homogeneity from these various organisms. Peptide sequencing of them could consequently not be performed. It is found, moreover, that the molecular masses of PYRases vary greatly according to the microorganisms from which they originate. As an example, there may be mentioned *Enterococcus faecium* PYRase, which possesses a molecular mass of approximately 42 kDa, whereas *Bacillus amyloliquefaciens* PYRase possesses a molecular mass of approximately 24 kDA.

These enzymes, apart from their known peptidase activity, constitute a major criterion for the differentiation of enterobacteria (Mutczyk and Szewczuk, J. Gen. Microbiol., 1970, 61, 9–13), from staphylococci (Mulzcyk and Szewczuk, J. Gen. Microbiol., 1970, 70, 383–384), as well as an important factor in presumption of Group A streptococci and enterococci (Ellner et al., J. Clin. Microbiol., 1985, 22, 880–881).

On studying the genetics of these enzymes, the Applicant discovered, surprisingly, that the nucleotide sequences coding for the PYRases are very different for each of the species of microorganism studied, and that, in addition, the genes coding for PYRases originating from different microbial organisms, though having very divergent nucleotide sequences, code, in fact, for proteins having very convergent peptide sequences.

A considerable homology is, in effect, observed between the peptide sequences of PYRases extracted, for example, from *Streptococcus pyogenes* and from *Bacillus subtilis*. This discovery is of twofold interest. On the one hand, the production of specific antibodies directed towards the highly homologous peptide sequences of PYRases provides reagents capable of detecting all microbial species capable of synthesizing a PYRase. On the other hand, nucleotide probes comprising fragments of the gene coding for the PYRase of a particular microbial species constitute specific reagents for the species in question.

The highly conserved peptide sequences present in the PYRases of various microbial species are those which correspond, in particular, to the peptides of formulae I to III given below. The subject of the present invention is hence a purified polypeptide containing at least one peptide sequence of at least six amino acids which is chosen from the peptide sequence shown in FIG. 3(SEQ ID NO:1), 5(SEQ ID NO:2), or 6(SEQ ID NO:3) possessing at least 40% homology with the peptide sequence shown in FIG. 3, 5 or 6.

The invention relates, in particular, to a purified polypeptide as defined above, characterized in that it possesses at least 20% identity with the peptide sequence shown in FIG. 3, 5 or 6.

The invention relates especially to a polypeptide as defined above, characterized in that it contains at least one peptide sequence of at least six amino acids which is chosen from the following sequences:

Glu—Arg—Val—Ala—Ile—Asn—X—X—Asp—Ala—Arg—Ile—Pro—Asp—Asn—X—Gly—X—Gln—Pro—Ile—Asp (SEQ ID NO: 4) (I);
Gly—X—X—Ala—X—Val—Ser—X—Thr—Ala—Gly—Thr—Phe—Val—Cys—Asn—X—X—X—Tyr (SEQ ID NO: 5) (II);
Leu—X—Thr—Gly—Phe—X—Pro—Phe (SEQ ID NO: 6) (III);

in which sequences X is an amino acid.

The meanings of X in the peptides I, II and III, respectively, are, in particular, given below for $Z_1$, $Z_2$, $Z_3$ and $Z_4$, and especially those which are readily identifiable in FIG. 9.

The invention relates, in particular, to a polypeptide containing a peptide sequence of at least six amino acids which is chosen from the following:

Gly—$Z_1$—$Z_1$—Ala—X—Val—Ser—$Z_2$—Thr—Ala—Gly—Thr—Phe—Val—Cys—
Asn—$Z_4$—$Z_1$—$Z_1$—Tyr (SEQ ID NO: 7) (IIa), and
Leu—$Z_1$—Thr—Gly—Phe—$Z_3$—Pro—Phe (SEQ ID NO: 8) (IIIa), in which sequences:

$Z_1$, each independently of one another, represents Ala, Val, Leu, Ile, Pro, Trp, Phe or Met;

$Z_2$, each independently of one another, represents Gly, Ser, Thr, Tyr, Gys, Ash or Gln;

$Z_3$, each independently of one another, represents Gly, Ser, Thr, Tyr, Cys, Ash, Gln, Ala, Asp or Glu; and $Z_4$, each independently of one another, represents Gly, Ser, Thr, Tyr, Cys, Ash, Gln, Lys, Arg or His.

The polypeptides of the invention can possess any number of amino acids greater than or equal to 6. The polypeptides of the invention are, in particular, the polypeptides having the formulae I to III, especially the polypeptides having the formulae Ia to IIIa, as well as the purified polypeptides or proteins containing at least the peptide sequence shown in FIG. 3, 5 or 6. The invention relates especially to a polypeptide having at least 40% homology with the polypeptide shown in FIG. 3, 5 or 6, as well as to a polypeptide having at least 20% identity, and in particular at least 30% identity, with one of the polypeptides of FIGS. 3, 5 and 6.

The invention also encompasses peptide-protein conjugates in which a polypeptide as defined above is linked to an antigenic protein, either directly through a peptide bond or via a spacer arm. Coupling using a spacer arm is carried out according to known methods. Such conjugates may be used in the preparation of specific antibodies directed towards a polypeptide or a protein containing an amino acid sequence chosen from the polylpeptide sequences defined above, including those of formulae I to III (or IIa and IIIa).

By administration of such conjugates to a host (mammal or bird), it is possible to obtain polyclonal antibodies capable of recognizing peptide sequences defined above, chosen, for example, from those of formulae I to III, and also to prepare, according to known methods, monoclonal antibodies specific for the peptide sequences.

Such antibodies, which also form part of the invention, make it possible, in particular, to detect bacterial proteins having PYRase activity. For this detection, the antibodies are used according to conventional immunoassay techniques. Specifically, using two monoclonal antibodies each recognizing a different peptide chosen, in particular, from the peptide sequences of formulae I to III, it is possible to perform an immunological test of detection of a protein having PYRase activity according to the one-step sandwich technique.

The subject of the invention is also a purified polynucleotide (nucleic acid fragment) coding for a polypeptide as defined above, including a polynucleotide coding for a peptide fragment chosen from the sequence of the peptides of formulae I to III (in particular Ia to IIIa), as well as a polynucleotide coding for a fragment of at least 6 amino acids which is chosen from the peptide sequence of FIG. 3, 5 or 6. The invention also relates to a fragment of a purified polynucleotide as defined above, this fragment having at least 10 nucleotides. The invention encompasses, in addition, the polynucleotides or fragments complementary to the polynucleotides or fragments which have just been obtained.

The invention relates especially to such a polynucleotide, chosen from the nucleotide sequences shown in FIGS. 3, 5 and 6, coding, respectively, for S.pyrogenes, B.subtilis and S.fluorescens PYRase.

The invention encompasses all native or recombinant genes coding for an enzyme possessing PYRase activity whose protein homology is at least 40% and/or identity at least 20% with S.pyrogenes, S.fluorescens or B.subtilis PYRase.

The subject of the invention is also a recombinant cloning or expression vector containing a polynucleotide as defined above, and a transformed living cell containing said recombinant vector, especially a cell which can be cultured in vitro, for example a bacterial cell.

The subject of the present invention is also the use of a nucleic acid fragment (polynucleotide) coding for an enzyme having pyrrolidone carboxylyl peptidase activity, possessing at least one of the peptide sequences I to III (or IIa and IIIa), for the overproduction of this enzyme according to genetic techniques, using any suitable recombinant expression vector, in particular a plasmid, inserted into a host cell, by culturing the host cell thus transformed, or alternatively for any genetic construction, such as the construction of a "reporter" gene, in a cloning vector of any kind, using at least a portion of the nucleic acid fragment coding for this enzyme. The invention also relates to a DNA or RNA nucleic acid probe, characterized in that it contains a sequence of at least 10 nucleotides (or at least 12 or at least 15 nucleotides) belonging to a polynucleotide according to the invention as has just been defined, or a sequence complementary to said sequence. Special mention may be made of the oligonucleotides referred to in the experimental part below. Such probes may be used as capture probes (for example bound to a solid support in a known manner, in particular by adsorbtion or covalently, or using a coupling agent), or may be linked to a label (or tracer agent), in a known manner, to constitute a detection probe, according to conventional hybridization techniques. Specifically, the probes containing nucleotide sequences chosen from those shown in FIGS. 3, 5 and 6 constitute specific detection probes for S.pyrogenes, B.subtilis and S.fluorescens, respectively.

These nucleic acid probes are used in a known manner in bacterial detection, identification or epidemiology.

The subject of the invention is also a method for the detection of a gene coding for a pyrrolidone carboxylyl peptidase in a microorganism, using at least one nucleic acid probe as defined above. Such a method may be carried out according to conventional techniques, for example by sandwich hybridization. A nucleic acid probe bound to a support may be used as a capture probe, and a labeled probe may be used as a detection probe.

As stated above, the cloning of a pcp gene coding for a PYRase is hence, in particular, of interest in making possible any form of overproduction of this enzyme, and exportation into the culture medium of said enzyme, onto which, for example, a signal sequence favoring protein excretion has been grafted by genetic engineering in a known manner. Recourse to the production of cloned enzymes thus makes it possible to decrease very considerably the operating costs of the processes of purification of the enzyme of interest. The invention hence enables pcp genes of various bacterial organisms to be cloned and sequenced, in particular in order to be able to overproduce a PYRase. This cloning may, for example, be carried out on the organisms for which the Applicant has demonstrated PYRase activity, namely: *Enterococcus faecalis, Enterococcus faecium, Enterococcus durans, Enterococcus avium, Enterococcus gallinarum, Enterococcus malodoratus, Enterococcus suis, Enterococcus sp., Lactococcus lactis, Lactococcus sp., Streptococcus equisimilis, Streptococcus sanguis, Streptococcus pneumoniae, Streptococcus agalactiae, Streptococcus porcinus, Streptococcus salivarius, Streptococcus uberis, Streptococcus acidominimus, Streptococcus boris, Streptococcus sp., Aerococcus viridans, Aerococcus sp., Micrococcus kristinae, Micrococcus luteus, Micrococcus lylae, Micrococcus varians, Micrococcus sp., Stomatococcus mucilaginosus, Stomatococcus sp., Gemella haemolysans, Gemella morbillorum, Gemella sp., Pseudomonas fluorescens, Pseudomonas sp., Citrobacter freundii, Citrobacter sp., Enterobacter cloacae, Enterobacter amnigenus, Enterobacter aerogenes, Enterobacter liquefaciens Enterobacter sp., Klebsiella aerogenes, Klebsiella pneumoniae, Klebsiella edwardsii, Klebsiella ozaenae, Klebsiella rhinoscleromatis, Klebsiella oxytoca, Klebsiella cloacae, Klebsiella sp., Serratia marcescens, Serratia grimesii, Serratia sp., Staphylococcus aureus, Staphylococcus capitis, Staphylococcus chromogenes, Staphylococcus gallinarum, Staphylococcus epidermis, Staphylococcus hominis, Staphylococcus hyicus, Staphylococcus lentus, Staphylococcus saprophyticus, Staphylococcus schleiferi, Staphylococcus warneri, Staphylococcus xylosus Staphylococcus lugdunensis, Staphylococcus simulans, Staphylococcus intermedius, Staphylococcus haemolyticus, Staphylococcus caprae, Staphylococcus carnosus, Staphylococcus cohnii, Staphylococcus kloosii, Staphylococcus sp., Neisseria mucosa, Neisseria sp., Bacillus megaterium, Bacillus subtilis, Bacillus cereus, Bacillus sp., Corynebacterium aquaticum, Corynebacterium bovis,* Corynebacterium group A, Corynebacterium group ANF, Corynebacterium group B, Corynebacterium group G1, Corynebacterium group G2, *Corynebacterium jeikeium, Corynebacterium kutscheri, Corynebacterium minutissimum, Corynebacterium pseudodiphteriticum, Corynebacterium striatum, Corynebacterium xerosis, Actinomyces pyogenes, Arcanobacterium haemolyticum, Brevibacterium sp., Erysipelothrix rhusiopathiae, Gardnerella vaginalis, Oerskovia spp., Rhodococcus equi.*

A few definitions of terms used in the present application are given below:

PYRase means a native or recombinant protein possessing pyrrolidone carboxylyl peptidase activity which is expressed before or after post-translational modifications; pcp gene(s) means native or recombinant gene coding for pyrrolidone carboxylyl peptidase (PYRase) originating from bacterial organisms;

"Reporter" gene corresponds to a coding unit whose expression product is readily assayable or detectable. The expression of a reporter gene makes it possible, in particular, to study the function or content of a nucleic acid sequence placed in an expression vector upstream of the gene, for example those of a promoter or operator;

Consensus sequence corresponds to the ideal sequence in which each position represents the base most often encountered on comparison of several sequences;

Underlined bases are the bases which correspond to the consensus sequences;

Canonical promoter denotes the consensus sequence of the promoter;

Transcripts are the products of DNA transcription;

Nucleic acid fragment means DNA or RNA fragment;

Homology relates to homologous amino acids, that is to say amino acids which have the same chemical properties such as polarity and/or hydrophobicity and/or basicity and/or acidity and/or neutrality. An amino acid is also considered to be homologous to another if their respective codons for the amino acid differ by only one base, termed degenerate;

Identity refers to strictly identical amino acids;

Cosmids refers to plasmids into which the Cos sites of phage lambda have been inserted; the resulting plasmid DNA can be encapsidated in vitro in phage particles;

Plasmid means extrachromosomal circular DNA capable of replicating autonomously; Phagemid means plasmid into which an origin of replication of a phage has been inserted; the resulting DNA can be encapsidated in vivo in phage particles; inclusivity results means the set of bacterial strains leading to the obtaining of a PCR amplification product using the oligonucleotides employed, or of a hybridization signal with the pcp probe for *S.pyogenes;*

Exclusivity results means the set of bacterial strains not leading to the obtaining of a PCR amplification product using the oligonucleotides employed, or of a hybridization signal with the pcp probe for *S.pyogenes.*

According to the invention, the cloning vectors can be plasmids such as: pBR322, pUC18/pUC19, pUC118/pUC119, pSP64/pSP65, pGEM-3/pGEM-4, pGEM-37, AN3, pBluescript M13 or the like. The cloning vectors according to the present invention may also be chosen from cosmids such as pJB8, c2RB, pCos1EMb1, pHC79, pTM, pMCS, pNNL, pHSG274, pWE15, Charomid9 or the like. The cloning vectors of the present invention can, in addition, be prokaryotic expression vectors such as bacterial expression vectors, or yeast expression vectors, or eukaryotic expression vectors such as mammalian expression vectors. The host cells can be eukaryotic or prokaryotic cells. Preferably, the host cells are prokaryotic cells; such as bacteria. Advantageously, bacterial host cells which do not express PYRase activity, such as *E. coli* cells, are chosen, but it is also possible to use bacterial host cells originally possessing PYRase activity, after carrying out a mutogenisis resulting in the disappearance of the PYRase activity in these bacteria. It is thus possible to clone *Pseudomonas fluorescens* PYRase in a mutant of this bacterium lacking PYRase activity. Preferably, according to the invention, *E. coli* is used as host cell.

BRIEF DESCRIPTION OF THE DRAWINGS

A better understanding of the invention will be gained on reading the detailed description which follows, reference being made to the attached figures

FIG. 5 (SEQ ID NO:2) shows the nucleotide sequence of the coding portion of the *Bacillus subtilis* pcp gene. The nucleotides are numbered from the 5' end to the 3' end of the antisense (untranscribed) strand. The amino acid sequence deduced from the nucleic acid sequence is indicated below the DNA sequence;

FIG. 6 (SEQ ID NO:6) shows the nucleotide sequence of the coding portion of the *Pseudomonas fluorescens* pcp gene. The nucleotides are numbered from the 5' end to the 3' end of the antisense (untranscribed) strand. The peptide sequence is indicated below the DNA sequence according to the three-letter code;

FIG. 7, which is used herein to refer to all of FIGS. 7A-1, 7A-2, 7A-3, 7B-1, 7B-2 and 7B-3 corresponds to a comparative analysis of the homology of the *Streptococcus pyogenes*, *Bacillus subtilis* and *Pseudomonas fluorescens* pcp genes (FIGS. 7B-1, 7B-2 and 7B-3) and of the corresponding proteins (FIGS. 7A-1, 7A-2 and 7A-3) by the establishment of comparison matrices. The numbering indicates, respectively, the nucleotide or amino acid residues. The data were established with the MacVector (IBI) (trade mark) sequence analysis software using the following parameters: (1) nucleic acid comparison: analysis window= 30 residues, minimum homology score=65%, rejection value=6 residues. (2) protein comparison: analysis window=8 residues, minimum homology score=50%, rejection value=2 residues;

FIG. 8, which is used herein to refer to FIGS. 8A and 8B, shows the comparison of the amino acid sequences of the proteins encoded by the *Streptococcus pyogenes* pcp gene (lower sequence) and (SEQ ID NO:10) that of *Bacillus subtilis* (upper sequence) (SEQ ID NO:9). In this figure, the amino acids are indicated by the three-letter code and the following alignment symbols are used: (l) corresponds to identical amino acids, (:) corresponds to highly homologous amino acids and (.) corresponds to amino acids possessing low homology, the amino acids which are not joined by a symbol corresponding to heterologous amino acids. The sequence discontinuities imposed by the optimal alignment are represented by dashes (−);

FIG. 9, which is used herein to refer to both of FIGS. 9A and 9B, shows the optimal alignment of the amino acid sequences of the proteins encoded by the pcp genes of *Streptococcus pyogenes* (upper sequence) (SEQ ID NO:11), *Pseudomonas fluorescens* (middle sequence) (SEQ ID NO:12) and *Bacillus subtilis* (lower sequence) (SEQ ID NO:13). In this figure, the amino acids are indicated by the three-letter code and the symbols and the numbering corresponds to the amino acid residues of the *Streptococcus pyogenes* protein. In this figure, the amino acids are indicated by the three-letter code and the conserved peptide units are boxed (shaded). The consensus common to the three peptide sequences (SEQ ID NO:14) is indicated in bold characters below the conserved regions, the letter "X" denoting the absence of identity of the amino acids. The sequence discontinuities imposed for producing the optimal alignment are represented by dashes (−)

DETAILED DESCRIPTION OF PREFERRED EMBODIMENTS

A shows the electrophoretic separation on denaturing polyacrylemide gel of the proteins synthesized in vivo by E.col K38/pGP1-2 possessing plasmid pT7-5 (lane 1), pPC39 (lane 2), pT7-6 (lane 3) and pPC40 (lane 4). Staining of the proteins is carried out with Coomassie blue; the arrow indicates the expression product of approximately 25 kDa relative to the molecular weight markers (M) (Bethesda Research Laboratories) (trade mark). B represents the corresponding autoradiograph of the gel. The exclusive labeling of the overexpressed protein of interest of pPC39 confirms the direction of transcription of the pcp gene shown in FIG. 1.

Unless specified, all the methods relating to the experiments which are presented below were carried out according to Sambrook et al. (Molecular cloning. A Laboratory Manual. Cold Spring Harbor Laboratory, Cold Spring Harbor, N.Y.).

Example 1: cloning of the pcp gene coding for
*Streptococcus pyogenes* PYRase

A library of genes of *Streptococcus pyogenes* strain D471 (Group A of Lancefield, type 6 protein M) (Scott and Fischetti, Science, 1983, 221, 758–760), which possesses PYRase activity, was constructed in *Escherichia coli* strain C600NR (λcI857) (Scott and Fischetti, Science, 1983, 221, 758–760). *S. pyogenes* chromosomal DNA, extracted according to the method of Chassy (Biochem. Biophys. Res. Comm., 1976, 68, 603–608), was partially digested with the restriction enzyme Mbo I in order to obtain a random series of fragments ranging from 30 to 50 kilobases (kb). The latter were inserted into cosmid pJB8 (Ish-Horowicz and Burke, Nucl. Acids Res., 1981, 9, 2989–2998) linearized by complete digestion using the endonuclease Bam HI. These recombinant vectors were introduced in vitro inside phage λ capsids (Hohn and Collins, Gene, 1980, 11, 291–298) using a Gigapack plus kit (Stratagene, trade mark). The resulting phages were used to transduce the strain C600NR, and bacterial colonies possessing the ampicillin resistance conferred by the cosmid were selected at 30° C.

These bacterial colonies were screened in situ on agar medium using the pyrrolidone carboxylyl peptidase test (Mulczyk and Szewczuk, J. Gen. Microb., 1970, 61, 9–13). Extraction of the recombinant plasmids from *Escherichia coli* clones possessing PYRase activity enabled plasmid pPC10 as shown FIG. 1, containing a 5-kb chromosomal DNA fragment of *S. pyogenes*, to be isolated. Introduction of pPC10 into *E. coli* JM83 bacteria (Yannish-Perron et al., Gene, 1985, 33,103–109) led to the production of transformants systematically possessing PYRase activity, confirming that the isolated DNA segment actually codes for this enzyme (Cleuziat et al., Mol. Microbiol., 1992, 6, 2051–2063).

Figure 1:
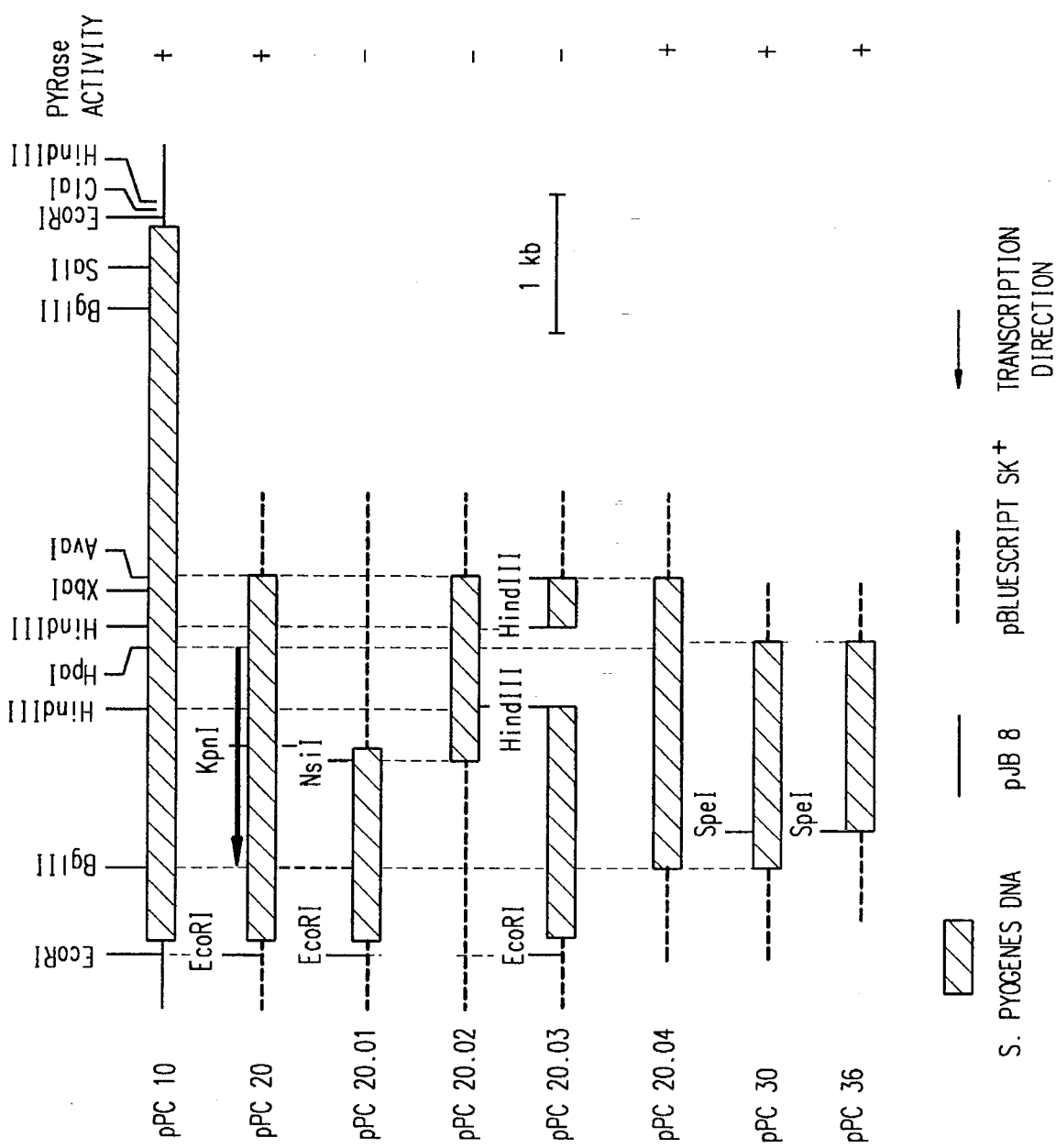
FIG. 1 illustrates diagrammatically the main steps of subcloning of the *Streptococcus pyogenes* pcp gene. In this figure, the partial restriction maps of plasmid pPC10 and its derivative are shown. The arrow indicates the location and the direction of transcription of the pcp gene, which is determined by the expression of the products of the 1.6-kb Bgl II-Hpa I fragment of pPC20 in the specific system phage T7 promoter/polymerase. The + symbols denote the presence of PYRase activity, and the − symbols the absence of activity.
Figure 2:
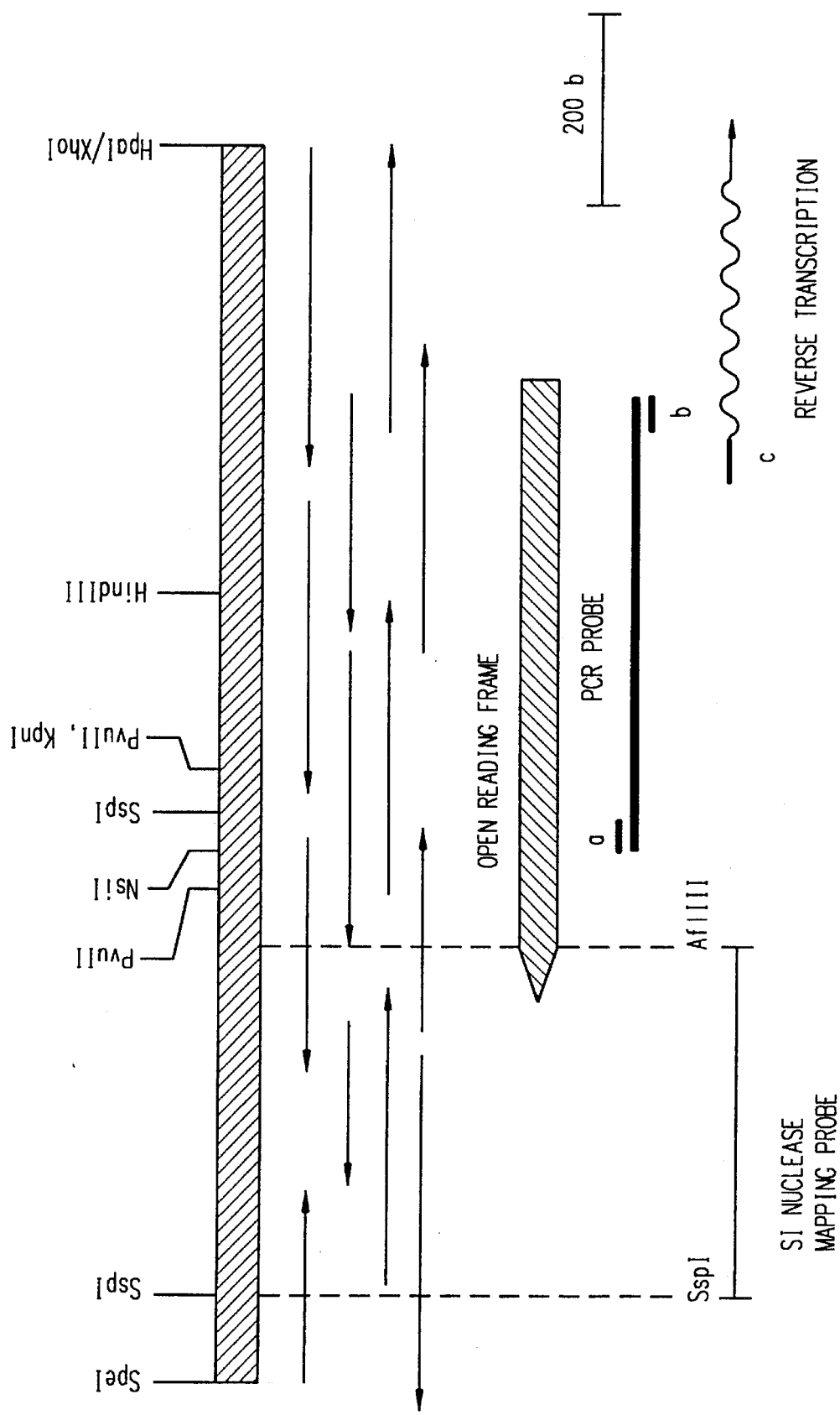
FIG. 2 illustrates diagrammatically the experimental approach used for the sequencing, hybridization and analysis of the pcp gene transcripts. Each arrow situated under the restriction map indicates the direction and length of a continuous sequence determination for obtaining the complete nucleotide sequence of the Hpa I-Spe I DNA fragment of pPC36 as shown in FIG. 1. The open reading frame identified and the pcp DNA probe synthesized by polymerization chain reaction with the oligonucleotides YR2 (a) and YU5 (b) are represented, respectively, by the hatched area and the bold lines. The location of the oligonucleotide YM1 (c) used for primer extension experiment and of the DNA probe for S1 nuclease mapping is shown in greater detail in FIG. 3.

Example 2: subcloning of the pcp gene coding for *Streptococcus pyogenes* PYRase Different endonucleases were used to establish a restriction map of the DNA fragment of interest contained in pPC10 (FIG. 1). This made it possible to localize more accurately the DNA region coding for the PYRase. The main steps in this subcloning are summarized in FIG. 1. Isolation and insertion of the Eco RI-Ava I fragment of pPC10 into the Eco RI-Sal I sites of the vector pBluescript KS⁺ (trade mark, Stratagene), leading to plasmid pPC20, permits detection of the PYRase activity in *E. coli* strain NM522 (Gough and Murray, J. Mol. Biol., 1983, 166, 1–19) transformed with this plasmid. According to the diagram of FIG. 1, plasmids pPC20.01, pPC20.02, pPC20.03, pPC30 and pPC36 were prepared and studied successively. The smallest DNA region conferring PYRase activity consists of a 1.3-kb Spe I-Hpa I restriction fragment (pPC36), the restriction map of which is detailed in FIG. 2.

Example 3: sequencing of the Spe I—Hpa I restriction fragment of pPC36

The complete nucleotide sequence of the two complementary strands of the Spe I—Hpa I fragment of plasmid pPC36 was determined by the chain termination method (Sanger et al., Proc. Natl. Acad. Sci. USA, 1977, 74, 5463–5467), according to the strategy described in FIG. 2, on double-stranded DNA templates. This sequence, described in FIG. 3, discloses the presence of a single open reading frame of 645 nucleotides. This open reading frame, the beginning of which is situated at the ATG initiation codon at position 285 and which terminates at the TAA stop codon located at position 930, codes for a 23135-Da protein composed of 215 amino acids and possessing a statistical isoelectric point of 7.3.

Example 4: analysis of the nucleotide sequence

This gene coding for pyrrolidone carboxylyl peptidase was designated pcp. It is preceded by a ribosome binding site (AAAGGA), the location and sequence of which are comparable to those described in other Gram-positive organisms (Moran et al., Mol. Gen. Genet., 1982, 186, 339–386). Two promoters (Pa and Pb) preceding the coding frame of pcp (FIG. 3) have been identified (Cleuziat, Doctorate ès Sciences Thesis: Institut National des Sciences Appliquées de Lyon, 1992, 157 p).

Example 5: analysis of the RNA transcripts

Figures 1, 7A:
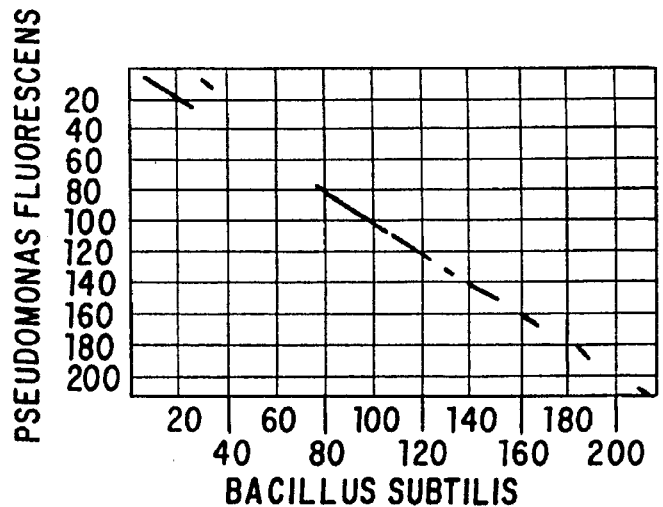
Figures 2, 7A:
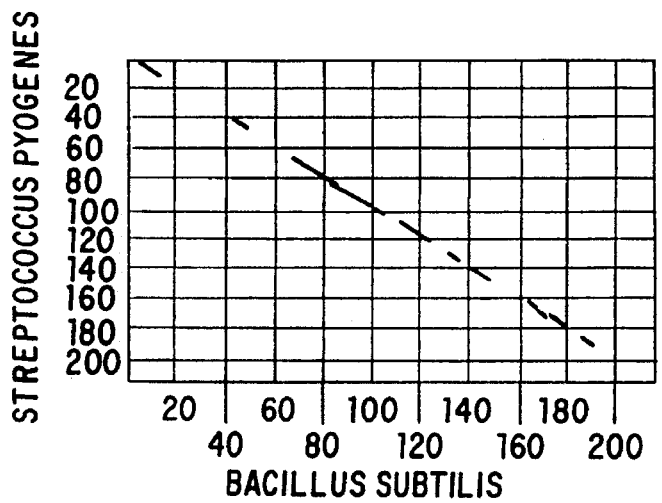
Figures 3, 7A:
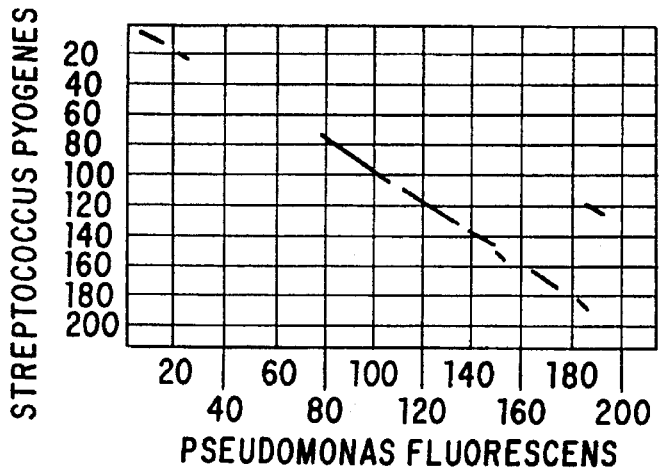
FIG. 3 (SEQ ID NO:1), which is used to refer to both of FIGS. 3A and 3B, shows the nucleotide sequence of the *Streptococcus pyogenes* pcp gene and its flanking regions. The nucleotides are numbered from the 5' end of the antisense (untranscribed) strand. The deduced amino acid sequence is indicated above the DNA sequence by the three-letter code. The transcription initiation and termination codons are boxed. The restriction sites of interest and the oligonucleotides mentioned in the text are shown. −10 and −35 regions of the two promoters ($P_a$ and $P_b$) as well as the presumed ribosome binding site (SD) are underlined. The inverted repeat sequences are symbolized by convergent arrows, and the stem-loop structure corresponding to the proposed transcription terminator is underlined in bold characters. +1 indicates the 5' (start) ends of the mRNA, determined by primer extension experiments. The 3' (stop) ends detected by S1 nuclease mapping are represented by asterisks below the sequence.
Figures 1, 7B:
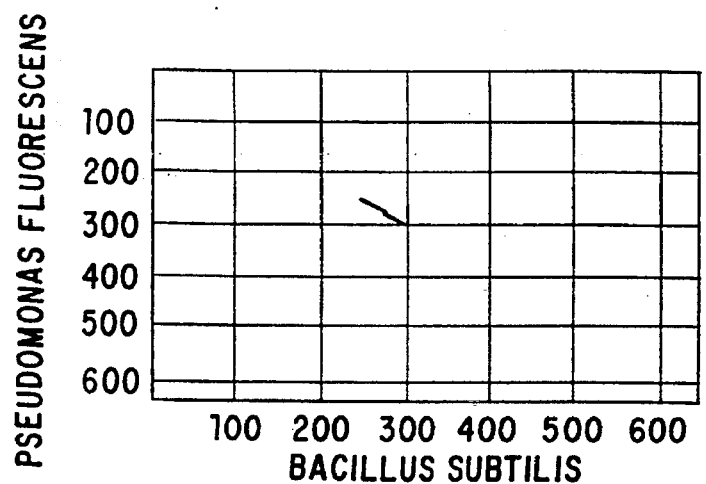
Figures 2, 7B:
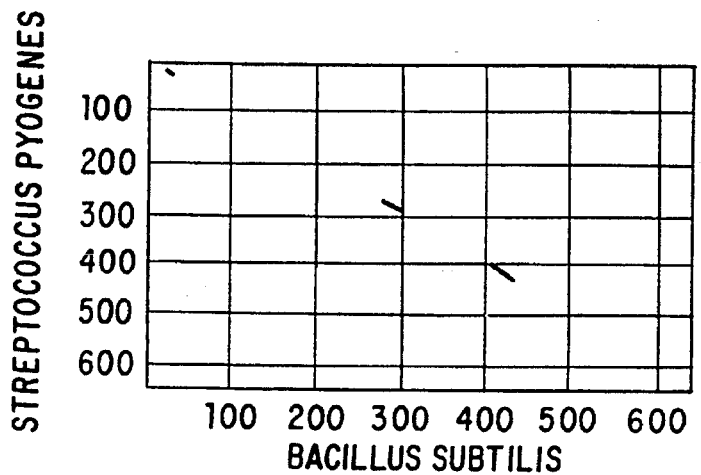
Figures 3, 7B:
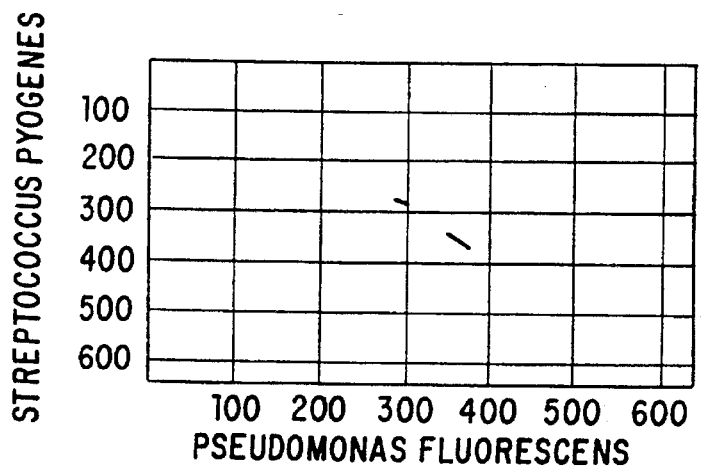

By carrying out primer extension experiments, it was possible to localize the 5' end of the pcp transcript, corresponding to the transcription start-site of this gene in the recombinant strain *E. coli* NM522/pPC30. For this purpose, the total RNA of this bacterium was extracted according to a method described by Shimotsu et al., (J. Bacteriol., 1986, 166, 466–471). The oligonucleotide YM1 ($^5$'dAATAGCT-TCGCCGCCAAAGGGATCAAAGCC$^3$') (SEQ ID NO:15), complementary to nucleotides 303 to 332 (FIG. 3), was labeled at its 5' end with [γ-$^{32}$P]-ATP (6000 Ci/mmol) with T4 polynucleotide kinase and hybridized under stringent conditions with the total RNA. Its extension with reverse transcriptase (FIG. 2) enabled two cDNAs to be detected, differing from one another by only one nucleotide and corresponding to a start of transcription situated on the G at position 257 or the T at position 258 (FIG. 3). The first position proves to be more in agreement with the fact that transcription generally starts on a purine base (A, G) and occasionally on a pyrimidine base (C, T) (Rosenberg and Court, Ann. Rev. Genet., 1979, 13, 319–353).

Two inverted repeat sequences were identified on the nucleotide sequence (FIG. 3). The shorter, situated within the A/T-rich region and partially overlapping the promoter sequences, constitutes a potential binding site for a regulatory protein (Gicquel-Sanzey and Cossart, EMBO J., 1982, 1, 591–595). The longer, situated 25 bases downstream of the TGA stop codon of pcp, is involved in the termination of transcription of pcp (Rosenberg and Court, Ann. Rev. Genet., 1979, 13, 319–353). Determination of the 3' end of the pcp transcript by the S1 nuclease mapping technique enabled the stem-loop structure responsible for the termination of transcription to be identified within this inverted repeat sequence. An Afl III-Ssp I restriction fragment of plasmid pPC36 (FIG. 2) was labeled at its 3' end using [α-$^{32}$P]-dCTP (3000 Ci/mmol) with the Klenow fragment of *Escherichia coli* DNA polymerase I. This probe of 353 nucleotides, overlapping the coding region over a zone of 21 bases (FIG. 3), was hybridized with the total RNA extracted from the recombinant *E. coli* bacterium obtained by transformation using plasmid pPC30. The whole was then subjected to the action of S1 nuclease according to defined conditions (Brakhage et al., Biochimie, 1990, 72, 725–734) in order to digest any single-stranded DNA fragment which is not protected by hybridization with the mRNA. Determination of the size of the fragments obtained consecutively under these conditions enabled it to be demonstrated that transcription stops between nucleotides 981 and 986 included in the nucleotide sequence (FIG. 3).

Figure 4:
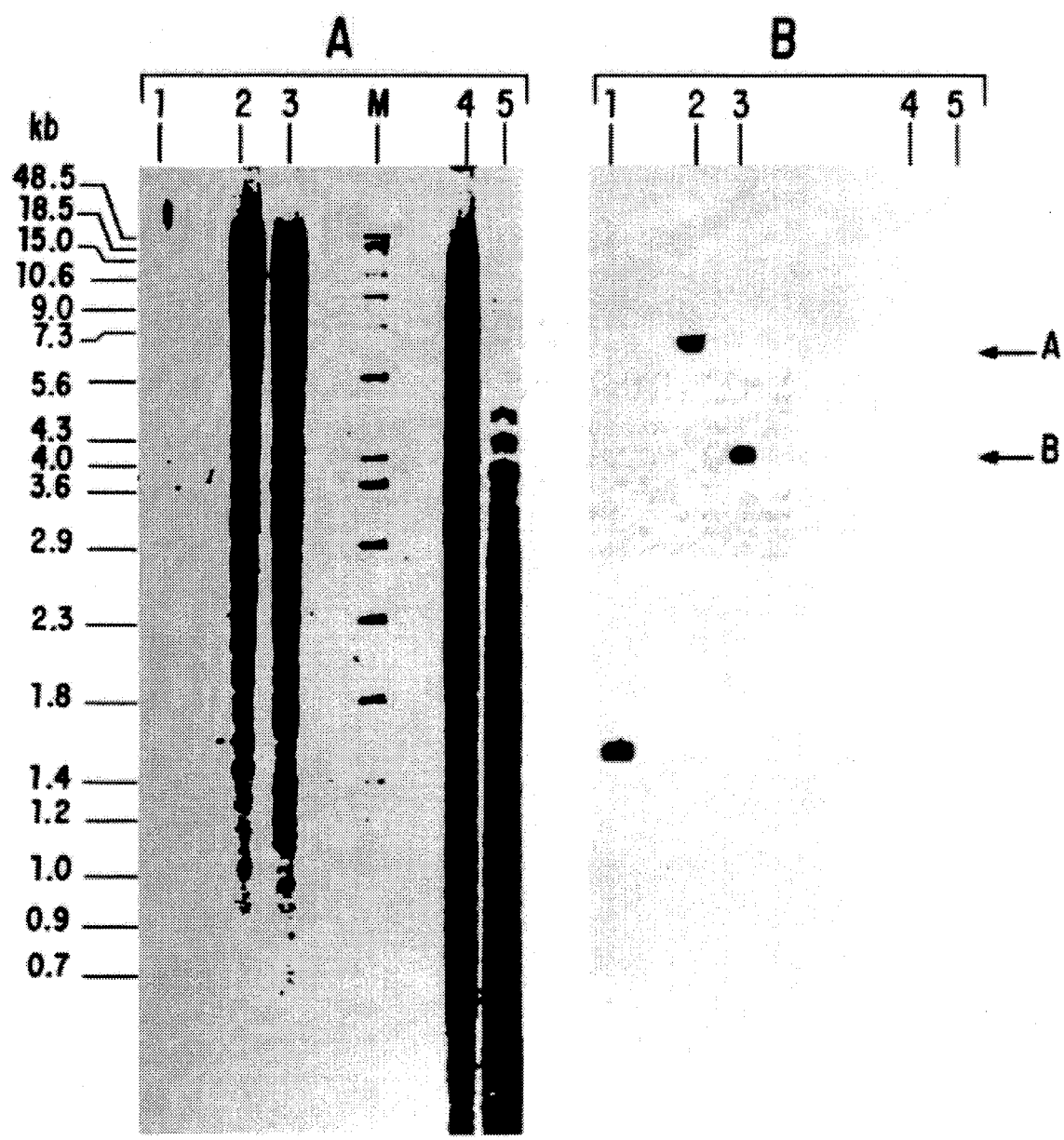
FIG. 4 shows the analysis by sucrose gel electrophoresis and hybridization according to Southern's method of the *Streptococcus pyogenes*, *Enteroccus faecalis* and *Bacillus subtilis* genome. A corresponds to the electrophoretic separation of the DNA fragments on 0.7% agarose gel. Plasmid pPC20, as shown in FIG. 1, is digested with the restriction endonucleases Bgl II and Hpa I (lane 1). *S. pyogenes* genomic DNA (approximately 50 μg/lane) was digested with Hpa I (lane 2) and Bgl II (lane 3). *E. faecalis* DNA (lane 4) and *B. subtilis* DNA (lane 5) are digested, respectively, with Hind III and Rsa I. The molecular weight scale (M) consists of Raoul II (Appligene) (trade mark). B corresponds to the autoradiograph of the Southern transfer hybridized with the pcp gene probe synthesized by PCR as shown in FIG. 2. The signal of the 1.6-kb restriction fragment (lane 1) constitutes the evidence of strict homology with the probe under stringent hybridization conditions. A hybridization signal is observed only in the case of S. pyogenes.

Example 6: Determination of the copy number of the pcp gene within the *Streptococcus pyogenes* genome Hybridization experiments according to Southern's method showed that the *S. pyogenes* genome comprises only one copy of the pcp gene. To do this, the DNA of this organism, extracted according to the method of Chassy (Biophys. Res. Comm., 1976, 68, 603–608), was digested with the restriction endonucleases Hpa I and Bgl II, which do not cut the pcp gene, and subjected to agarose gel electrophoresis. Transfer of the genetic material was carried out by capillarity onto a nylon membrane before hybridization with a double-stranded DNA probe, synthesized by polymerization chain reaction (PCR), comprising the larger part of the coding region of the pcp gene. PCR was carried out as described by Saiki et al., (Science, 1988, 239, 487–491) on a double-stranded plasmid DNA template (pPC30) using AmpliTaq (Perkin Elmer Cetus, trade mark), employing the oligonucleotides YR2 (5'dACAG-GCTTTGATCCCTTTGG3') (SEQ ID NO:16) and YU5 corresponding to positions 300 to 319 and complementary to 759 to 778 of the sequence, respectively (FIG. 3). This 479-base pair fragment was purified on agarose gel and radioactively labeled with [α-$^{32}$P]-dCTP (3000 Ci/mmol), using the "random priming" kit (Boehringer, trade mark). The hybridization and washing conditions, termed stringent, were carried out in a known manner in order to permit hybridization of the pcp probe only with a completely homologous DNA target. To this end, a control was set up by double digestion of plasmid pPC20 with the endonucleases Hpa I and Bgl II. FIG. 4 shows that a positive hybridization signal was obtained for the 1.6-kb fragment containing the pcp gene, while the 4-kb fragment corresponding to the cloning vector and to the DNA regions of S. pyogenes flanking pcp did not disclose any signal. The presence of a single hybridization signal in the case of each digestion of DNA confirms that pcp is a single-copy gene in the S. pyogenes genome. The size of the bands observed (6.8 kb and 4.1 kb) is in complete agreement with the restriction map of the DNA region coding for the PYRase.

The pcp gene did not disclose any homology with the nucleotide and protein sequences present in the databases (Genbank, version No. 68 of Jun. 15, 1991).

Example 7: analysis and comparison of pcp genes originating for different bacterial species The work performed on the Streptococcus pyogenes pcp gene was extrapolated to other bacterial organisms possessing PYRase activity.

From a library of Bacillus subtilis genes constructed in Escherichia coli in plasmid pMK4 (Débarbouillé et al., FEMS Microbiol. Lett. 1987, 41, 137–140), the cloning and molecular characterization of the Bacillus subtilis pcp gene were carried out according to the techniques described above for S. pyogenes. The sequence of the coding portion of this gene together with that of the protein for which it codes are indicated in FIG. 5. The B. subtilis pcp gene possesses a length of 645 nucleotides and codes for a protein of 215 amino acids of theoretical molecular weight equal to 23777 Da (Awadé et al., FEBS Lett., 1992, 305, 67–73).

No homology of nucleotide or protein sequence could be determined by comparison with the databases of existing sequences. Similarly, there is very little homology between the S. pyogenes pcp gene and that of B. subtilis, although these genes are both composed of exactly 645 nucleotides. FIG. 7 shows that, despite a complete absence of homology from the nucleotide standpoint (B), the corresponding proteins are extremely conserved (A). The primary structure of the PYRases of S. pyogenes and of B. subtilis were compared (FIG. 8): the alignment of these two proteins is based on the "BestFit" program (University of Wisconsin) using the algorithm of Devereux et al., (Nucl. Acid Res., 1984, 12, 387–395). The two proteins contain the same number of amino acids (215 residues). Their total sequences possess 47.5% identity and greater than 66% homology, indicating a very high degree of conservation of these proteins. Some zones can have up to 80% identity and greater than 87% homology, as is the case with the unit of 41 amino acids Gln-Pro-Asp-Ala-Val-Leu-Cys-Ile-Gly-Gln-Ala-Gly-Gly-Arg-Thr-Gly-Leu-Thr-Pro-Glu-Arg-Val-Ala-Ile-Asn-Gln-AsP-AsP-Ala-Arg-Ile-Pro-Asp-Asn-Glu- Gly-Asn-Gln-Pro-Ile-Asp (SEQ ID NO:17) (residues 59 to 99 inclusive) of S. pyogenes PYRase. The regions situated in the vicinity of the cysteine residues (S. pyogenes Cys 65, Cys 141 and Cys 156) are also highly conserved, in particular the units Gly-Leu-Pro-Ala-Ser-Val-Ser-Asn-Thr-Ala-Gly-Thr-Phe-Val-Cys-Asn-His-Leu-Met-Tyr (SEQ ID NO:18) (residues 129 to 146 inclusive) (75% identity, 85% homology) and Cys-pro-Asn-Ala-Lys-Ala-Gly-Phe-Met-His-Ile-Pro-Phe-Met (SEQ ID NO:19) (residues 156 to 169 inclusive) (42% identity and 93% homology). Other, shorter regions possess large homologies: the fragments of 11 amino acids Lys-Ile-Leu-Val-Thr-Gly-Phe-Asp-Pro-Phe-Gly and Glu-Val-Pro-Thr-Val-Phe (SEQ ID NO:20) (residues 2 to 12 inclusive) (72% identity, 100% homology) and of 6 amino acids (residues 39 to 44 inclusive) (66% identity, 100% homology).

Moreover, following the construction of a library of genes of Pseudomonas fluorescens strain A32 (Gügi et al., J. Bacteriol., 1991, 173, 3814–3820) in the host Escherichia coli DH5α in plasmid pUC19, the cloning and molecular characterization of the Pseudomonas fluorescens pcp gene were also carried out according to the techniques described above for S. pyogenes. The sequence of the coding portion of this gene together with that of the protein for which it codes are indicated in FIG. 6. The Pseudomonas fluorescens pcp gene possesses a length of 639 nucleotides and codes for a protein of 213 amino acids of 22436 Da.

No homology of nucleotide or protein sequence could be determined by comparison with the databases of existing sequences. Similarly, there is very little homology between the Pseudomonas fluorescens pcp gene and those of S. pyogenes and B. subtilis, although these genes are composed of an almost identical number of nucleotides. FIG. 7 shows that, despite a complete absence of homology from the nucleotide standpoint (B), the corresponding proteins are extremely homologous (A). The PYRase of P. fluoroscens possesses globally 47% identity and 66% homology with that of B. subtilis, and 39% identity and 62% homology with that of S. pyogenes. The structure of the bacterial PYRases hence appears to be highly conserved from the peptide standpoint, although the nucleotide sequences coding for the corresponding peptides are very divergent.

Determination of the optimal alignment using the program mentioned above from the three PYRases characterized makes it possible to bring out the major peptide units of these enzymes (FIG. 9). Three highly conserved units, included in those determined above between B. subtilis and S. pyogenes (FIG. 8), are clearly seen (FIG. 9), from which the consensus of identity (bold character) may be deduced. With respect to the numbering of S. pyogenes PYRase, the units involved are Leu-Val-Thr-Gly-Phe-Asp-Pro-Phe (residues 4 to 11 inclusive) (75% identity and 100% homology), Glu-Arg-Val-Ala-Ile-Asn-Gln-Asp-Asp-Ala-Arg-Ile-Pro-Asp-Asn-Glu-Gly-Asn-Gln-Pro-Ile-Asp (SEQ ID NO:21) (residues 78 to 99 inclusive) (82% identity and 86% homology) and Val-Ser-Asn-Thr-Ala-Gly-Thr-Phe-Val-Cys-Asn (SEQ ID NO:22) (residues 132 to 142 inclusive) (91% identity and 100% homology). This unit, the most highly conserved of all, contains the cystein residue common to the three PYRases (Streptococcus pyogenes Cys 141). It is probably the one involved in the catalytic site of this family of enzymes.

Example 8: detection of pyrrolidone carboxylyl peptidase by antibodies

Polyclonal antibodies specifically directed towards one of the peptides Gln-Pro-Asp-Ala-Val-Leu-Cys-Ile-Gly-Gln-Ala-Gly-Gly-Arg-Thr-Gly-Leu-Thr-Pro-Glu-Arg-Val-Ala-Ile-Asn-Gln-AsP-AsP-Ala-Arg-Ile-Pro-Asp-Asn-Glu- Gly-Asn-Gln-Pro-Ile-Asp (SEQ ID NO:23), Gly-Leu-Pro-Ala-Ser-Val-Ser-Asn-Thr-Ala-Gly-Thr-Phe-Val-Cys-Asn-His-Leu-Met-Tyr (SEQ ID NO:24), Cys-Pro-Asn-Ala-Lys-Ala-Gly-Phe-Met-His-Ile-Pro-Phe-Met (SEQ ID NO:25), Lys-Ile-Leu-Val-Thr-Gly-Phe-Asp-Pro-Phe-Gly (SEQ ID NO:26) and Glu-Val-Pro-Thr-Val-Phe described above in Example 7 were produced. To do this, these peptides, previously synthesized and purified, were separately grafted onto the protein KLH (high molecular weight immunogenic molecule): 5 mg of protein and 5 mg of peptide are brought into contact in a volume of 2 ml of 50 mM phosphate buffer pH 7.5, and coupling is carried out by adding 1 ml of 20 mM glutaraldehyde. The conjugates obtained were dialyzed overnight against PBS buffer. Rabbits were then immunized by intramuscular injection of 1 ml of the solution obtained above, added to 1 ml of Freund's complete adjuvant. A booster was performed one month after the initial injection, and a volume of blood of 20 ml was withdrawn one week after this booster. After coagulation, the serum fraction is filtered and immunoglobulins are purified on a Sepharose protein A affinity column (Pharmacia, trade mark) according to the protocol recommended by the supplier. The specificity of the antibodies obtained was tested by conventional immunological detection methods (ELISA). For this purpose, each peptide described above, the immunogenic molecule KLH and bovine serumalbumin (BSA) were adsorbed individually on the wells of microtitration plates (Nunc, trade mark). By bringing each category of purified polyclonal antibodies into contact, and detecting the latter with goat anti-rabbit antibodies coupled to peroxidase (Sigma, trade mark), it was shown that the antibodies obtained recognize specifically and exclusively the peptides with which the immunization was performed. No cross-reaction was observed between, on the one hand each category of antibodies, and on the other hand the other peptides which were not used for obtaining them. The antibodies obtained also made it possible to detect pyrrolidone carboxylyl peptidase in *Streptococcus pyogenes, Bacillus subtilis* and also other bacteria possessing such an enzymatic activity. Since this enzyme is located in the intracellular compartment, its detection in the microorganisms involved prior lysis of the cells by physical or chemical means. In this case, the lysis was carried out by disintegration of the cell membranes under the action of ultrasound (sonication). By taking up and washing the sonicate in 50 mM phosphate buffer pH 7.5, the presence of the enzyme could be determined by the immunological method described above. No positive reaction could be observed using organisms not possessing enzymatic activity, confirming the specificity of the purified antibodies. These results hence confirm the conservation and specificity of the peptide units studied within the pyrrolidone carboxylyl peptidases (PYRases) originating from microorganisms.

Example 9: detection of *Streptococcus pyogenes* (Group A β-hemolytic streptococci)

The detection of Streptococcus pyogenes is of very great importance in clinical bacteriology, since this organism is the source of numerous and varied pathologies in man. Group A β-hemolytic streptococci, which correspond to the species *Streptococcus pyogenes,* can be responsible for many disorders such as pharyngitis, sore throat, sinusitis, osteomyelitis, cellulitis and various skin disorders, endocarditis, meningitis, etc. They are known above all to be responsible for scarlet fever, the two main secondary manifestations of which are acute rheumatic fever (ARF) and acute glomerulonephritis (AGN) (Delmas and Freney, Lyon Pharmaceutique, 1989, 40, 353–369). Some of these pathologies can be lethal (Bartter et al., Arch. Intern. Med., 1987, 148, 1421–1424).

At present, the identification of Group A streptococci in medical microbiology involves study of hemolysis on blood agar, testing for a Lancefield Group A antigen or for physiological and biochemical characters (API 20 STREP identification gallery, marketed by the company bioMérieux). The need to identify the streptococci responsible for acute infections rapidly has led to the development of agglutination techniques (Malbrunot et al., Pathologie Biologie, 1990, 35, 665–668) permitting the direct recognition of Group A antigens (Slidex-strepto kit, BioMérieux) from the primary culture colonies. These methods can nevertheless make it obligatory to perform enrichment and isolation steps sometimes necessitating up to 48 hours, and they possess limits from the standpoint of sensitivity.

The use of DNA probes decreases the time needed for establishment of the diagnosis by direct and sensitive detection of microbes from biological samples. In effect, DNA probes may be used for the detection of particular organisms in biological samples as described in U.S. Pat. No. 4,358,535 in the name of Falkow et al. Probes for Group A streptococci have already been proposed, such as oligonucleotides for the type 1 protein M gene of *Streptococcus pyogenes* (Podbielski et al., Med. Microbiol. Immunol. 1990, 179, 255–262) or the type A exotoxin gene (Yu and Ferretti, Infect. Immun., 1989, 57, 3715–3719). These probes are, however, specific for targets which define several subgroups within Group A streptococci, and hence do not make it possible to detect the whole of the species; hence there does not exist at present a DNA probe for the detection of *Streptococcus pyogenes*.

The feasability and specificity of detection or of identification of Group A streptococci has been demonstrated below using an experimental protocol employing PCR or Southern hybridization.

a) study by PCR

Different pairs of primers covering the region of the pcp gene were tested in respect of the specificity of obtaining an amplified fragment from genomic DNA of various bacteria. These pairs of primers are shown in Table 1 below.

TABLE 1

| Pairs of oligonucleotides used in PCR | | | |
|---|---|---|---|
| Pair[a] | Name | Position[b] | Size of the product[c] |
| 1: ACAGGCTTTGATCCCTTTGG (SEQ ID NO: 16) | YR2 | 300–319 | |
| 2: TTCTGGCGTTAGTCCAGTCC (SEQ ID NO: 27) | YU3 | 499–518 | 219 |

TABLE 1-continued

| Pairs of oligonucleotides used in PCR | | | |
|---|---|---|---|
| Pair[a] | Name | Position[b] | Size of the product[c] |
| 1: ACAGGCTTTGATCCCTTTGG (SEQ ID NO: 16) | YR2 | 300–319 | |
| 2: TATCAGGAATGCGAGCATCG (SEQ ID NO: 24) | YU8 | 539–558 | 259 |
| 1: ACAGGCTTTGATCCCTTTGG (SEQ ID NO: 16) | YR2 | 300–319 | |
| 2: TGCATAAACCCAGCTTTGGC (SEQ ID NO: 29) | YU5 | 759–778 | 479 |
| 1: TTGCCAGCAACCATTCATGG (SEQ ID NO: 30) | YR4 | 360–379 | |
| 2: AGAAACAGAAGCAGGAAGCC (SEQ ID NO: 31) | YU9 | 664–683 | 324 |
| 1: TTGCCAGCAACCATTCATGG (SEQ ID NO: 30) | YR4 | 360–379 | |
| 2: TGCATAAACCCAGCTTTGGC (SEQ ID NO: 29) | YU5 | 759–778 | 419 |
| 1: AAAATCTGCCGATGTGCTCC (SEQ ID NO: 32) | YR5 | 419–438 | |
| 2: AGAAACAGAAGCAGGAAGCC (SEQ ID NO: 31) | YU9 | 664–683 | 265 |
| 1: AAAATCTGCCGATGTGCTCC (SEQ ID NO: 32) | YR5 | 419–438 | |
| 2: TGCATAAACCCAGCTTTGGC (SEQ ID NO: 29) | YU5 | 759–778 | 360 |
| 1: CTTTGTATTGGGCAAGCTGG (SEQ ID NO: 33) | YR6 | 474–4 93 | |
| 2: AGAAACAGAAGCAGGAAGCC (SEQ ID NO: 31) | YU9 | 664–683 | 210 |
| 1: CTTTGTATTGGGCAAGCTGG (SEQ ID NO: 33) | YR6 | 474–493 | |
| 2: TACTGGCAAACTATACCCGC (SEQ ID NO: 34) | YU4 | 1075–1094 | 621 |
| 1: TGCTCGCATTCCTGATAACG (SEQ ID NO: 35) | YR7 | 542–561 | |
| 2: TGCATAAACCCAGCTTTGGC (SEQ ID NO: 29) | YU5 | 759–778 | 237 |
| 1: TGCTCGCATTCCTGATAACG (SEQ ID NO: 35) | YR7 | 542–561 | |
| 2: TACTGGCAAACTATACCCGC (SEQ ID NO: 34) | YU4 | 1075–1094 | 553 |
| 1: ATCAAAGCGATGGTTGCTGC (SEQ ID NO: 36) | YR8 | 630–649 | |
| 2: TACTGGCAAACTATACCCGC (SEQ ID NO: 34) | YU4 | 1075–1094 | 465 |
| 1: ATCAAAGCGATGGTTGCTGC (SEQ ID NO: 36) | YR8 | 630–649 | |
| 2: CCCTATCTCAATGCTTAACG (SEQ ID NO: 37) | YU1 | 1297–1316 | 687 |
| 1: TCAAAAATCTGCCGATGTGC (SEQ ID NO: 38) | YF1 | 416–435 | |
| 2: AGGAAGCCCAGCCTGATGAA (SEQ ID NO: 39) | YF2 | 652–671 | 256 |

[a]sense oligonucleotide (corresponding to the sequence); 2: antisense oligonucleotide (reverse and complementary to the sequence). The nucleotide sequence is indicated from the 5' end to the 3' end
[b]the numbering corresponds to that of the sequence described in FIG. 3.
[c]the size of the amplification product is indicated in base pairs.

The bacteria studied (international collection strains and strains of clinical origin) were isolated and cultured on suitable agar medium.

A 5 ml ampoule of heart-brain broth is inoculated with a bacterial clone originating from a 12-hour culture on agar medium, and is incubated at 37° C. under conditions appropriate to each organism. The concentration of the bacteria in the exponential growth phase is determined by measuring the optical density at 590 nm, and a volume corresponding to a quantity of $10^8$ bacteria (approximately 100 μl) is centrifuged for 5 minutes at 14,000 rpm in a sterile microtube. The bacterial pellet is washed with 200 μl of physiological saline (0.9% NaCl), centrifuged again and resuspended in 100 μl of Tween 20 buffer (0.45% in sterile distilled $H_2O$). The sample is then heated to 100° C. for 5 minutes) in order to lyse the bacteria, and then cooled on ice or frozen for subsequent use. 10 μl of bacterial lysate, equivalent to the DNA originating from approximately $10^7$ bacteria, are used per PCR test.

The composition of the reaction mixture used for the PCR is strictly that described by Saiki et al., (Science, 1988, 239, 487–491). The reaction was carried out using AmpliTaq (Perkin Elmer Cetus, trade mark) on a Thermal Reactor apparatus (Hybaid, trade mark) according to the following temperature cycle:

(92° C., 5 min)

[(60° C., 30 sec), (75° C., 30 sec), (95° C., 15 sec)] 40 times (60° C., 30 sac)

(75° C., 10 min)

1/10th of the amplification product (10 μl) is analyzed by electrophoresis on 2% agarose gel relative to molecular weight markers.

No difference could be observed regarding the specificity of the oligonucleotide pairs used for the amplification of a DNA fragment from the bacterial genome: the specificity results obtained for each bacterial strain studied were the same irrespective of the pair used.

The quantitative results nevertheless vary slightly according to the pair studied. The oligo-nucleotide pair YF1-YF2 is the one which enabled the best amplification yields to be obtained. These oligonucleotides prove especially advantageous from the standpoint of sensitivity of detection of the microorganisms by molecular hybridization techniques. The qualitative results described for YF1-YF2 in Tables 2 and 3 below, collating, respectively, the bacterial species which did or did not give a positive amplification signal, can be fully extrapolated to the other pairs of oligonucleotides.

TABLE 2

Inclusivity results

| LRA Collection | International collection | Bacterial species | PYRase activity | Hybridization pcp probe* | PCR amplification** | VIDAS detection*** |
|---|---|---|---|---|---|---|
| | JRS4 | Streptococcus pyogenes M6 | + | + | + | 2306 |
| 77-01-085 | NCTC 8191 | Streptocoque groupe A | + | + | + | 693 |
| 84-05-026 | | Streptocoque groupe A | + | + | + | 519 |
| 77-01-083 | NCTC 10879 | Streptococcus pyogenes | + | + | + | 981 |
| 89-11-070 | | Streptococcus pyogenes | + | + | + | 704 |
| 89-11-071 | | Streptococcus pyogenes | + | + | + | 3153 |
| 83-02-114 | | Streptocoque groupe A | + | + | + | 5707 |
| 89-11-070 | | Streptocoque groupe A | + | + | + | 6287 |
| 78-06-155 | | Streptococcus pyogenes | + | + | + | 2682 |
| 76-11-002 | ATCC 12202 | Streptococcus pyogenes | + | + | + | 1929 |
| 77-01-028 | ATCC 12203 | Streptococcus pyogenes | + | + | + | 2013 |
| 77-01-029 | NCTC 10085 | Streptococcus pyogenes | + | + | + | 2527 |
| 77-01-030 | NCTC 8306 | Streptococcus pyogenes | + | + | + | 1991 |

*Hybridization results obtained using the double-stranded DNA probe corresponding to the coding frame of the *Streptococcus pyogenes pcp* gene
**Results of PCR amplification using the pair of primers YF1-YF2
***Results of enzymatic (alkaline phosphatase) activity following capture and detection of the amplification products

TABLE 3

Exclusivity results

| LRA Collection | International collection | Bacterial species | PYRase activity | Hybridization pcp probe* | PCR amplification** | VIDAS detection*** |
|---|---|---|---|---|---|---|
| | CG110 | Enterococcus faecalis | + | − | − | 5 |
| 83-10-064 | | Enterococcus faecalis | + | − | − | 5 |
| 89-10-032 | | Enterococcus faecium | + | − | − | 4 |
| 84-07-114 | | Enterococcus durans | + | − | − | 6 |
| 89-10-033 | | Enterococcus avium | + | − | − | 7 |
| 87-12-068 | | Enterococcus gallinarum | + | − | − | 6 |
| 84-10-087 | | Enterococcus malodoratus | + | − | − | 8 |
| 89-09-060 | | Enterococcus suis I | + | − | − | 6 |
| 90-02-014 | | Streptococcus uberis | − | − | − | 7 |
| 86-03-031 | | Streptococcus equisimilis | + | − | − | 9 |
| 76-11-006 | ATCC 35666 | Streptococcus equisimilis | − | − | − | 5 |
| 89-04-053 | ATCC 12401 | Streptococcus agalactiae | − | − | − | 8 |
| 78-11-148 | NCTC 10234 | Streptococcus suis II | − | − | − | 7 |
| 80-02-036 | NCTC 7864 | Streptococcus sanguis II | + | − | − | 5 |
| 77-01-036 | NCTC 6177 | Streptococcus zooepidemicus | − | − | − | 5 |
| 84-11-031 | | Streptococcus salivarius | − | − | − | 9 |
| 85-10-113 | | Streptococcus pneumoniae | + | − | − | 8 |
| 78-04-060 | NCTC 7465T | Streptococcus pneumoniae | − | − | − | 5 |
| 89-04-053 | | Group B streptocoque | − | − | − | 7 |
| 77-01-032 | NCTC 9828 | Group B streptocoque | − | − | − | 5 |
| 77-09-006 | NCTC 10228 | Group E streptocoque | − | − | − | 6 |
| 86-12-029 | | Group G streptocoque | − | − | − | 9 |
| 77-01-039 | | Group G streptocoque | − | − | − | 8 |
| 77-01-038 | NCTC 9603 | Group G streptocoque | − | − | − | 8 |
| | | Aerococcus viridans | + | − | − | 9 |
| 89-10-001 | | Aerococcus viridans | + | − | − | 11 |
| 78-11-159 | | Aerococcus viridans | + | − | − | 8 |
| 75-15-060 | ATCC 25571 | Micrococcus kristinae | + | − | − | 10 |
| 89-08-091 | | Lactococus lactis ssp. cremoris | − | − | − | 12 |
| 89-09-022 | | Lactococcus lactis ssp. lactis | − | − | − | 7 |
| 89-06-176 | | Stomatococcus mucilaginosus | + | − | − | 8 |
| 89-01-032 | | Listeria sp. | − | − | − | 15 |
| | C304 | Corynebacterium glutamicum | − | − | − | |
| 89-04-074 | | Pseudomonas fluorescens | + | − | − | 10 |
| 89-06-024 | | Psuedomonas fluorescens | + | − | − | 7 |
| 89-06-025 | | Pseudomonas fluorescens | − | − | − | 9 |
| 88-06-067 | | Shigella sp. | − | − | − | 10 |
| | P4X | Escherichia coli K-12 | − | − | − | 8 |
| 83-09-123 | | Escherichia vulneris | − | − | − | 10 |
| 73-08-010 | ATCC 8090 | Citrobacter freundii | + | − | − | 4 |
| 76-03-117 | | Citrobacter freundii | + | − | − | 6 |
| 73-08-013 | ATCC 13047 | Enterobacter cloacae | + | − | − | 6 |
| 75-08-036 | ATCC 13048 | Enterobacter aerogenes | + | − | − | 6 |

TABLE 3-continued

Exclusivity results

| LRA Collection | International collection | Bacterial species | PYRase activity | Hybridization pcp probe* | PCR amplification** | VIDAS detection*** |
|---|---|---|---|---|---|---|
| 89-09-015 | | Enterobacter aerogenes | + | − | − | 8 |
| 81-09-011 | ATCC 33072 | Enterobacter amnigenus | + | − | − | 7 |
| 85-05-027 | | Klebsiella pneumoniae | + | − | − | 7 |
| 75-01-109 | | Klebsiella oxytoca | + | − | − | 10 |
| 75-09-007 | ATCC 810 | Serratia marcescens | + | − | − | 10 |
| 85-01-018 | ATCC 29909 | Serratia grimesii | + | − | − | 10 |
| 75-09-008 | ATCC 25923 | Staphylococcus aureus | + | − | − | 9 |
| 87-12-083 | ATCC 43809 | Staphylococcus lugdenensis | + | − | − | 7 |
| 75-15-313 | ATCC 27848 | Staphylococcus simulans | + | − | − | 8 |
| 82-02-100 | ATCC 29663 | Staphylococcus intermedius | + | − | − | 9 |
| 75-15-306 | ATCC 29970 | Staphylococcus haemolyticus | + | − | − | 10 |
| 90-04-012 | ATCC 13102 | Neisseria meningitidis | − | − | − | 8 |
| 76-11-014 | | Neisseria mucosa | + | − | − | 8 |
| 86-06-009 | ATCC 19695 | Neisseria mucosa | − | − | − | 10 |
| 87-12-074 | | Bacillus megaterium | + | − | − | 8 |
| 78-02-084 | NCTC 10400 | Bacillus subtilis | + | − | − | 6 |
| 78-02-085 | NCTC 10320 | Bacillus cereus | + | − | − | 15 |

*Hybridization results obtained using the double-stranded DNA probe corresponding to the coding frame of the Streptococcus pyogenes pcp gene
****results of PCR amplification using the pair of primers YF1-YF2
***Results of enzymatic (alkaline phosphatase) activity following capture and detection of the amplification products Tables 2 and 3 giving, respectively, the inclusivity and exclusivity results show that the proposed oligonucleotides systematically and exclusively detect Group A streptococci (Streptococcus pyogenes). The diversity and location of the oligonucleotides on the coding portion of the gene and on its flanking regions prove that the region of the pcp gene is a region of the genome which is very specific to this bacterial species and hence favorable to the development of DNA probes for its detection in biological samples.

These tables demonstrate that the presence of a hybridization signal is independent of that of a PYRase phenotype, since bacteria other than S. pyogenes possessing this activity do not interfere in the detection of this microbe.

This amplification product of 256 base pairs obtained using the oligonucleotide pair YF1-YF2 may be visualized extremely rapidly and sensitively by an automated non-radioactive detection system based on sandwich hybridization (Dunn and Hassel, Cell, 1977, 12, 23–36). This system employs two non-overlapping oligonucleotides which correspond to the same DNA strand of the amplified fragment; the first, bound to a solid phase, is a capture probe for the amplification product, and the second, linked to alkaline phosphatase, serves as a detection probe (Jablonski et al., Nucl. Acids Res., 1986, 14, 6115–6128). After denaturation, hybridization and washing, detection is carried out by fluorescence using the substrate umbelliferyl phosphate. Tables 2 and 3 present the results of measurement of relative enzymatic activity, obtained using the oligonucleotide pair YF3 (5'dCAGCTTATTTTTCAACCTTGCC3') (SEQ ID NO:40 ) and YF4 (5'dCAAAGCGATGGTTG-CTGCCA3') (SEQ ID NO:41) corresponding to positions 607 to 628 and 632 to 651 of the pcp sequence (FIG. 3), used, respectively, as detection and capture probe, on a VIDAS (registered trade mark, marketed by the company bioMérieux) automated laboratory apparatus. Any activity less than or equal to 50 units corresponds to a negative result, comparable to the background of a control assay not including amplified DNA, while an activity above 500 units denotes the presence of the desired amplification product. The figures observed corroborate the qualitative results of testing for the amplification product after electrophoretic separation of a fraction of the reaction medium, and confirm the specificity of detection of Group A streptococci with these probes (Cleuziat et al., Proceedings of the Conference on Taxonomy and Automated Indentification of Bacteria, Prague, 1992, 70–73).

b) study by hybridization with genomic DNA

The genomic DNA of the bacteria studied above (international collection strains and strains of clinical origin) and listed in Tables 2 and 3 was extracted according to the method of Chassy cited above following their culture in a suitable liquid medium. Each DNA (quantity equivalent to approximately $10^{12}$ bacteria) was deposited on a nylon membrane using a vacuum filtration apparatus, then denatured and fixed on a membrane as described by Sambrook et al. (Molecular cloning. A Laboratory Manual. Cold Spring Harbor Laboratory, Cold Spring Harbor, N.Y.). These DNAs were then hybridized with a double-stranded DNA probe corresponding exactly to the coding frame of the Streptococcus pyogenes pcp gene under conditions permitting its hybridization only to a completely homologous target sequence, as described above. This probe was synthesized by PCR as described above, using the oligonucleotide primers 5'dATGAAAATTCTTGTAACAGGC3' (SEQ ID NO:42) corresponding to positions 285 to 305, and 5'dGTGAG-TAGCGCCCCCTAC3' (SEQ ID NO:43) complementary to positions 912 to 929 of the sequence of the Streptococcus pyogenes pcp gene (FIG. 3). The hybridization results are indicated in Tables 2 and 3. They demonstrate that the probe consisting of the whole of the Streptococcus pyogenes pcp gene permits the specific and exclusive detection of all strains of Streptococcus pyogenes (Group A β-hemolytic streptococci). No non-specific cross-reaction is observed with any of the other bacterial species, in particular those possessing PYRase activity, which demonstrates that the whole of the Streptococcus pyogenes pcp gene is a very specific genetic marker for this species. All or part of the sequence of the Streptococcus pyogenes pcp gene hence constitutes a specific detection probe for this species.

c) study by Southern hybridization

The genomic DNA of the bacteria *S. pyogenes* JRS4 (spontaneous streptomycin-resistant mutant of D471), *E. faecalis* CG110 (Gawron-Burke and Clewell, Nature, 1982, 300, 281–284) and *B. subtilis* 168 (Lepesant et al., Mol. Gen. Genet., 1972, 118, 135–160) is extracted according to the Chassy method cited above. These DNAs are subjected, respectively, to complete digestion with the restriction endonucleases Hpa I or Bgl II, Hind III and Rsa I. The resulting fragments are separated by agarose gel electrophoresis and transferred onto a nylon membrane according to Southern's method. This membrane is then hybridized with the PCR probe covering the larger part of the pcp gene, under conditions permitting its hybridization only with a completely homologous target sequence, as described above.

No hybridization signal is observed (FIG. 4) with the genome of the bacteria *Enterococcus faecalis* and *Bacillus subtilis*, in contrast to *Streptococcus pyogenes* which discloses the presence of a single hybridization band, the size of which confirms the established restriction map of the DNA region coding for the PYRase. This result hence shows that the whole of the pcp gene may be used as a DNA probe for the specific detection of Group A streptococci, and that any nucleotide sequence of sufficient length and of any location originating from this gene may also be used for this purpose.

The hybridization results corroborate those obtained by amplification. DNA extracted from the bacteria *E. faecalis* and *B. subtilis* does not give rise to cross-hybridization phenomena, although these organisms both possess PYRase activity. This demonstrates that there is no homology between the gene coding for the PYRase of these bacteria and the *S. pyogenes* pcp gene.

Example 10: overproduction of PYRase

PYRase is of paramount importance in the field of chemistry and biochemistry. Its activity makes it possible, in effect, to liberate terminal $NH_2$ groups which are blocked by a pyroglutamic residue, thereby making it possible to carry out the peptide sequencing procedure by the Edman sequential degradation method (Acta Chem. Scan, 1950, 4, 283–293).

Figure 10:
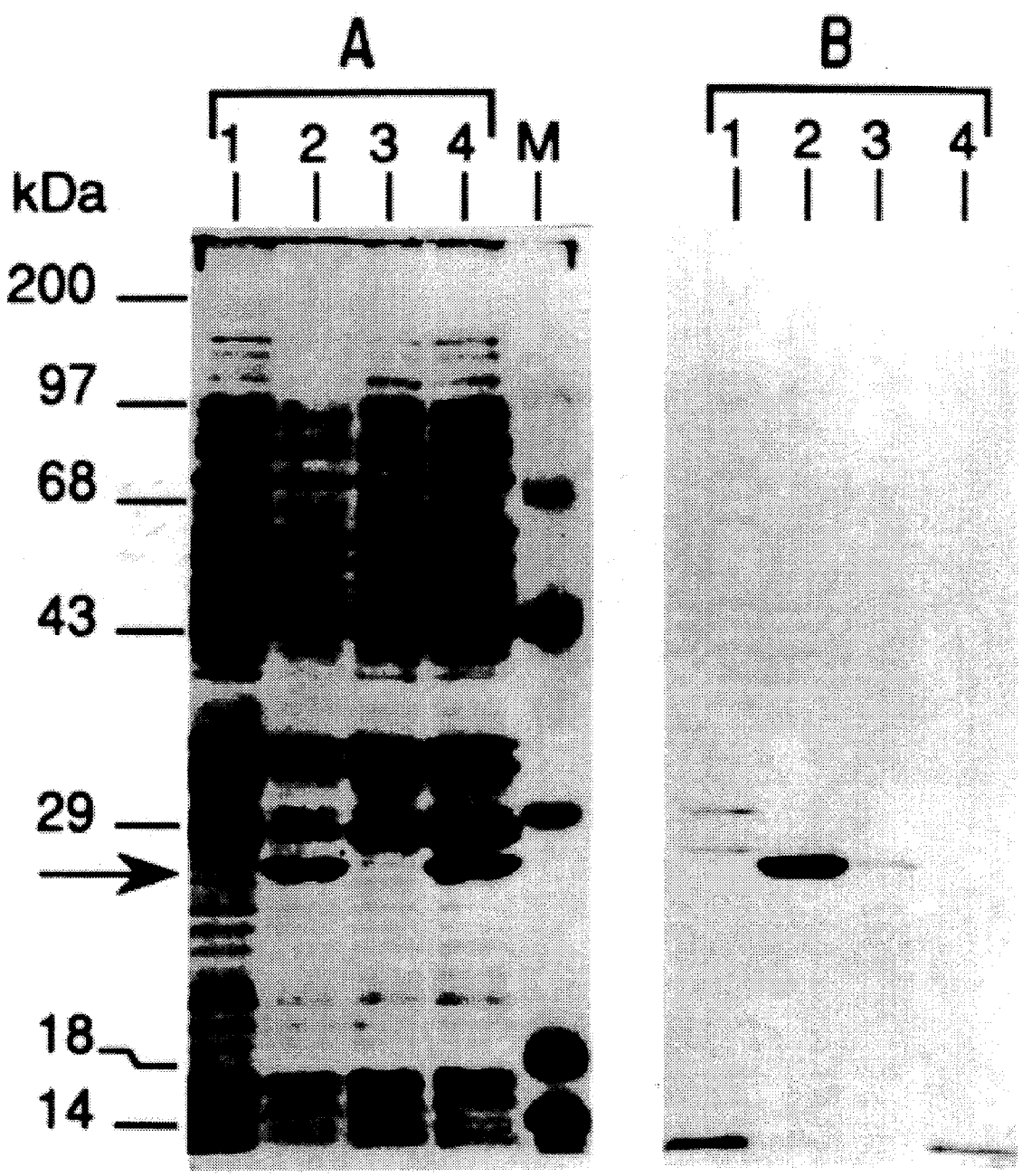
FIG. 10 represents an analysis of the expression products of the DNA coding for PYRase activity by the phage T7 promoter/polymerase system.

The 1.6-kbHpa I-Bgl II fragment originating from plasmid pPC20 (FIG. 1) was inserted into the expression vectors pT7-5 and pT7-6 (Tabor and Richardson, Proc. Natl. Acad. Sci. USA, 1985, 82, 1074–1078), which differ from one another in the orientation of the multiple cloning site situated downstream of the bacteria phage T7 promoter. The resulting plasmids, pPC39 and pPC40, respectively, were introduced into *E. coli* strain K38 (Russel and Model, J. Bacteriol., 1985, 159, 1034–1039) containing the compatible plasmid pGP1-2 (Tabor and Richardson, Proc. Natl. Acad. Sci. USA, 1985, 82, 1074–1078). After growth of the bacteria at 30° C. in a selective medium, the synthesis of RNA polymerase of phage T7 from pGP1-2 is induced by thermal shock at 42° C for 20 min. The bacterial RNA polymerase is then inhibited by adding rifampicin (200 µg/ml), leading to exclusive transcription of the pcp gene placed downstream of the phage T7 promoter. The product resulting from translation of the specifically transcribed RNA is visualized by means of the in vivo incorporation of L-[$^{35}$S]methionine (1000 Ci/mmol) added at the required time. The cells are thereafter lysed and their protein content is analyzed on denaturing 12.5% polyacrylamide gel (FIG. 10). Expression of the pcp gene under its own promoter from plasmids pPC39 and pPC40 makes it possible, as a result of the high copy number of these plasmids per bacterium, to obtain a significant quantity of PYRase, the apparent molecular weight of which is estimated at 26 kDa. The expressed enzyme proves to be greatly preponderant among the total cell proteins (FIG. 10). The expression of a labeled 26 kDa protein corresponding to PYRase from pPC39 shows that insertion of the pcp gene in the transcription direction imposed by the phage T7 promoter enables the product of this gene to be overproduced specifically. This overproduction permits the purification to homogeneity of a large quantity of PYRase per unit bacterial dry weight, by means of a chromatographic process involving only one step (Awadé et al., FEBS Lett., 1992, 308, 70–74). Likewise, it was possible to overexpress the *Bacillus subtilis* pcp gene which has been characterized, in order to overproduce the PYRase of this organism in *E. coli* using the phage T7 promoter/polymerase system described above. This approach also permits the pure protein to be obtained by a one step chromatographic purification process (Gonzales and Awadé, J. Chromatogr., 1992, 584, in the press).

We claim:
1. Purified polypeptide consisting of a peptide sequence consisting of part or all of a sequence selected from the group consisting of:
  amino acid residues 4–11 of SEQ ID NO: 11;
  amino acid residues 6–13 of SEQ ID NO: 13;
  amino acid residues 5–12 of SEQ ID NO: 12;
  amino acid residues 78–99 of SEQ ID NO: 11;
  amino acid residues 81–102 of SEQ ID NO: 13;
  amino acid residues 81–102 of SEQ ID NO: 12;
  amino acid residues 127–146 of SEQ ID NO: 11;
  amino acid residues 130–149 of SEQ ID NO: 13; and
  amino acid residues 130–149 of SEQ ID NO: 12; wherein said part of said sequence is at least six amino acids long.
2. Antibodies capable of specifically binding peptide sequences chosen from those which are defined in claim 1.
3. Purified polynucleotide coding for a peptide sequence selected from the group consisting of:
  amino acid residues 4–11 of SEQ ID NO: 11;
  amino acid residues 6–13 of SEQ ID NO: 13;

amino acid residues 5–12 of SEQ ID NO: 12;
amino acid residues 78–99 of SEQ ID NO: 11;
amino acid residues 81–102 of SEQ ID NO: 13;
amino acid residues 81–102 of SEQ ID NO: 12;
amino acid residues 127–146 of SEQ ID NO: 11;
amino acid residues 130–149 of SEQ ID NO: 13; and
amino acid residues 130–149 of SEQ ID NO: 12; or of a polynucleotide sequence complementary to said polynucleotide.

4. Recombinant cloning or expression vector, characterized in that said vector contains a polynucleotide as defined in claim 3.

5. Transformed cell it containing a recombinant vector as defined in claim 4.

6. Nucleic acid probe, characterized in that said probe consists of a sequence of at least 10 nucleotides of a polynucleotide as defined in claim 3, or a sequence complementary to said sequence.

7. Nucleic acid probe according to claim 6, characterized in that said probe is bound to a solid support.

8. Nucleic acid probe according to claim 7, characterized in that said probe is bound by adsorption or covalently.

9. Nucleic acid probe according to claim 7, characterized in that said probe is bound via a coupling agent.

10. Nucleic acid probe according to claim 6, characterized in that said probe is labeled using a tracer agent.

11. Method for the detection of a gene coding for a pyrrolidone carboxylyl peptidase in a microorganism using at least one nucleic acid probe, comprising using a nucleic acid probe as defined in claim 6.

12. Detection method according to claim 11, characterized in that said probe is bound to a support and is used as a capture probe.

13. Detection method according to claim 11, characterized in that said probe is labeled using a tracer agent and is used as a detection probe.

14. Method of preparing a recombinant vector comprising inserting a polynucleotide as defined in claim 3 into an appropriate cloning vector.

15. Method of preparing a transformed cell comprising transforming a cell with the recombinant vector according to claim 14.

16. A method for detecting anti-Pyrase antibodies in a sample, comprising the steps of:

contacting a polypeptide as defined in claim 1 with a sample under conditions permitting the formation of a complex between the polypeptide and anti-Pyrase antibodies, and detecting the presence of any said complex.

17. A method for detecting a gene coding for a pyrrolidone carboxylyl peptidase in a microorganism, comprising the steps of:

contacting under hybridizing conditions a nucleic acid probe as defined in claim 6 with a sample containing genomic material from a microorganism, and detecting the presence of any hybrid duplex.

* * * * *